(12) United States Patent
Berger

(10) Patent No.: US 8,691,529 B2
(45) Date of Patent: Apr. 8, 2014

(54) INCREASING PROTEIN PRODUCTION BY INCREASING ABC50 EXPRESSION OR ACTIVITY

(75) Inventor: Stuart A. Berger, Toronto (CA)

(73) Assignee: University Health Network, Toronto, Ontario (CA)

( * ) Notice: Subject to any disclaimer, the term of this patent is extended or adjusted under 35 U.S.C. 154(b) by 46 days.

(21) Appl. No.: 13/318,985

(22) PCT Filed: May 5, 2010

(86) PCT No.: PCT/CA2010/000681
§ 371 (c)(1),
(2), (4) Date: Dec. 16, 2011

(87) PCT Pub. No.: WO2010/127444
PCT Pub. Date: Nov. 11, 2010

(65) Prior Publication Data
US 2012/0094329 A1    Apr. 19, 2012

Related U.S. Application Data

(60) Provisional application No. 61/175,642, filed on May 5, 2009.

(51) Int. Cl.
C12P 21/06       (2006.01)
(52) U.S. Cl.
USPC ............................................. 435/69.1
(58) Field of Classification Search
USPC .......................................... 435/69.1
See application file for complete search history.

(56) References Cited

FOREIGN PATENT DOCUMENTS

WO           03/040296 A2    5/2003

OTHER PUBLICATIONS

Chloupkova et al. 2007; Expression of 25 human ABC transporters in yeast Pichia pastoris and characterization of the purified ABCC3 ATPase activity. Biochemistry. 46:7992-8003.*
Richard M. et al. ABC50, a novel human ATP-binding cassette protein found in tumor necrosis factor-alpha-stimulated synoviocytes. Genomics. 1998;53:137.
Tyzack J.K. et al. ABC50 interacts with eukaryotic initiation factor 2 and associates with the ribosome in an ATP-dependent manner. J Biol Chem. 2000;275:34131.
Paytubi S. et al. The N-terminal region of ABC50 interacts with eukaryotic initiation factor eIF2 and is a target for regulatory phosphorylation by CK2. Biochem J. 2008;409:223.
Soboloff J. et al. Sustained ER Ca2+ Depletion Suppresses Protein Synthesis and Induces Activation-enhanced Cell Death in Mast Cells. J Biol Chem.2002;277:13812.
Zhang Y. et al. Inhibition of Ca2+ influx is required for mitochondrial reactive oxygen species-induced endoplasmic reticulum Ca2+ depletion and cell death in leukemia cells. Mol Pharmacol. 2006;70:1424.
Soboloff J. et al. Sensitivity of myeloid leukemia cells to calcium influx blockade. Application to bone marrow purging. Exp Hematol. 2002;30:1219.
Zhang Y. et al. Purging of contaminating breast cancer cells from hematopoietic progenitor cell preparations using activation enhanced cell death. Breast Cancer Res Treat. 2002;72:265.
Hacker D.L. et al. Recombinant Protein Production Yields from Mammalian Cells: Past, Present, and Future. BioPharm International. 2008.
Yu Y. et al. Mitochondrial regulation by c-Myc and hypoxia-inducible factor-1 alpha controls sensitivity to econazole. Mol Cancer Ther. 2008;7:483.
Zhang Y. et al. Increased calcium influx and ribosomal content correlate with resistance to endoplasmic reticulum stress-induced cell death in mutant leukemia cell lines. J Biol Chem. 2004;279:6507.
Prashar Y. et al. Analysis of differential gene expression by display of 3' end restriction fragments of cDNAs. Proc Natl Acad Sci USA. 1996;93:659.
Moenner M. et al. Integrated endoplasmic reticulum stress responses in cancer. Cancer Res. 2007;67: 10631.
Zhang K. et al. Kaufman RJ. From endoplasmic-reticulum stress to the inflammatory response. Nature. 2008;454:455.
Mayer C. et al. mTOR-dependent activation of the transcription factor TIF-IA links rRNA synthesis to nutrient availability. Genes Dev. 2004;18:423.
Xiao L. et al. Coordination of Ribosomal Protein and Ribosomal RNA Gene Expression in Response to TOR Signaling. Curr Genomics. 2009; 10:198.
Mayer C. et al. The nucleolus as a stress sensor: JNK2 inactivates the transcription factor TIF-IA and down-regulates rRNA synthesis. Genes Dev. 2005; 19:933.
Ota M. et al. Two critical genes (HLA-DRB1 and ABCF1)in the HLA region are associated with the susceptibility to autoimmune pancreatitis. Immunogenetics. 2007;59:45.
Wilde D.B. et al. Evidence implicating L3T4 in class II MHC antigen reactivity; monoclonal antibody GK1.5 (anti-L3T4a) blocks class II MHC antigen-specific proliferation, release of lymphokines, and binding by cloned murine helper T lymphocyte lines. J Immunol. 1983;131:2178.
Dull T. et al. A third-generation lentivirus vector with a conditional packaging system. J Virol. 1998;72:8463.
Grynkiewcz G. et al. A new generation of Ca2+ indicators with greatly improved fluorescence properties. J Biol Chem. 1985;260:3440.
Lievremont J.P. et al. BiP, a major chaperone protein of the endoplasmic reticulum lumen, plays a direct and important role in the storage of the rapidly exchanging pool of Ca2+. J Biol Chem. 1997;272:30873.
Paytubi, S. et al., ABC50 promotes translation initiation in mammalian cells, Journal of Biological Chemistry, Sep. 4, 2009, vol. 284, No. 36, pp. 24061-24073.
Morrison, S. et al., Production and characterization of genetically engineered antibody molecules, Clinical Chemistry, Sep. 1988, vol. 34, No. 9, pp. 1668-1675.

* cited by examiner

Primary Examiner — Karen Cochrane Carlson
(74) Attorney, Agent, or Firm — Bereskin & Parr LLP; Camela DeLuca

(57) ABSTRACT

The disclosure provides methods and materials for increasing the expression of a protein of interest such as an antibody by a cell ABC50 expression or activity is increased which increases expression of the protein or antibody of interest. The disclosure also provides methods and materials for increasing the sensitivity of a cell to an endoplasmic reticulum stress agent such as Econazole by decreasing the level of ABC50.

79 Claims, 10 Drawing Sheets

A

B

INCREASING PROTEIN PRODUCTION BY INCREASING ABC50 EXPRESSION OR ACTIVITY

CROSS-REFERENCE TO RELATED APPLICATIONS

This application is a national phase entry of PCT/CA2010/000681, filed May 5, 2010, which claims priority from U.S. Provisional patent application serial number 61/175,642 filed May 5, 2009 each of these applications being incorporated herein in their entirety by reference.

INCORPORATION OF SEQUENCE LISTING

A computer readable form of the Sequence Listing "10723-385_SL.txt" (34,083 bytes), submitted via EFS-WEB and created on Nov. 4, 2011, is herein incorporated by reference.

FIELD OF THE DISCLOSURE

The disclosure relates to methods and compositions for protein production and specifically to methods and compositions for increasing hybridoma antibody production.

BACKGROUND OF THE DISCLOSURE

ABC50 (aka ABCF1) is a member of the ATP Binding Cassette (ABC) family of proteins. ABC50 was first identified as a Tumor Necrosis Factor α-inducible gene in synoviocytes [1], and then re-discovered as a protein that purifies with the translation initiation factor eIF2 [2]. Biochemically, ABC50 stimulates formation of complexes between eIF2, GTP and Met-tRNA, implicating it in translation initiation and control. ABC50 is a unique member of the ABC family in that it lacks transmembrane domains. Recently Paytubi et al. showed that the N-terminal region was responsible for eIF2 binding [3]. Binding was found to be regulated by Casein Kinase 2 phosphorylation in this domain. Overexpression of ABC50 into HEK293 cells was not observed to boost protein expression [3].

Econazole (Ec) is an imidazole antifungal that also induces endoplasmic reticulum (ER) stress by promoting ER $Ca^{2+}$ depletion. Ec's mechanism of action involves both $Ca^{2+}$ influx blockade and stimulation of ER $Ca^{2+}$ release [4]. The latter effect is mediated by reactive oxygen species (ROS) generation at the mitochondria [5]. Some cancer cells are extraordinarily sensitive to Ec [6, 7].

The market for therapeutic proteins is currently on the order of $60 Billion worldwide. The largest component of this market is recombinant monoclonal antibodies but also includes other protein classes such as cytokines, growth factors such as insulin, coagulation factors, vaccine subunits and therapeutic enzymes. The diagnostic market is similarly estimated to be $40 Billion worldwide and a significant fraction of this market employs recombinant proteins including monoclonal antibodies. Finally, recombinant proteins for research purposes also represent a large and growing use for recombinant proteins.

It was recently estimated that about half of the 140 recombinant proteins on the market are produced in mammalian cells [8]. Given the requirement for large amounts of protein, particularly in the therapeutic setting, there is clearly a need for optimizing natural and recombinant protein production.

SUMMARY OF THE DISCLOSURE

An aspect of the disclosure includes a method of producing a protein of interest in a cell comprising increasing the expression or activity of a ABC50 protein or a fragment thereof having eIF2 binding activity; and effecting the expression of the protein of interest.

In an aspect, the disclosure provides a method of producing a heterologous protein of interest in a cell comprising increasing the expression or activity of a ABC50 protein or a fragment thereof having protein synthesis increasing activity and/or eIF2 binding activity; and effecting the expression of the protein of interest.

In another aspect, the disclosure provides a method of producing an antibody of interest or fragment thereof in a cell capable of expressing an antibody comprising increasing the expression or activity of an ABC50 protein or a fragment thereof having protein synthesis increasing activity and/or eIF2 binding activity.

Another aspect relates to a method of increasing expression of a heterologous protein of interest in a cell expressing the protein of interest, comprising increasing the expression or activity of an ABC50 protein or a fragment thereof having protein synthesis increasing activity and/or eIF2 binding activity.

Yet another aspect relates to a method of increasing expression of an antibody of interest in a cell expressing the antibody of interest, comprising increasing the expression or activity of an ABC50 protein or a fragment thereof having protein synthesis increasing activity and/or eIF2 binding activity.

In an embodiment, the expression or activity of ABC50 protein or a fragment thereof is increased by introducing a heterologous ABC50 polynucleotide encoding ABC50 protein or a fragment thereof operatively linked to a promoter.

In another embodiment, the expression or activity of ABC50 protein or a fragment thereof is increased by contacting the cell with increasing concentrations of Econazole (Ec), and detecting increased expression or activity of ABC50 protein.

In an embodiment, the cell comprises a heterologous polynucleotide encoding the protein of interest operatively linked to a promoter.

In another embodiment, the expression or activity of ABC50 protein or a fragment thereof is increased and the expression of the protein of interest is effected by introducing a vector comprising a polynucleotide encoding ABC50 protein or a fragment thereof, and a heterologous polynucleotide of the protein of interest, wherein the polynucleotides are operatively linked to one or more promoters.

In another embodiment, effecting the expression of the protein of interest comprises contacting the cell with an inducer that induces expression of the protein of interest or induces expression of ABC50.

In a further embodiment, the ABC50 protein comprises SEQ ID NO: 1, 2 or 5; or a protein with at least 90%, 95%, 99% or 99.5% identity with SEQ ID NO:1, 2 or 5.

In an embodiment, the method results in increased specific cellular expression and/or production of the protein of interest in comparison to a control cell expressing the protein of interest wherein: the control cell does not have increased expression of an ABC50 protein or a fragment thereof having protein synthesis increasing activity and/or eIF2 binding activity.

In another embodiment, the method results in increased specific cellular expression and/or production of the antibody of interest in comparison to a control cell expressing the antibody of interest wherein the control cell does not have increased expression of an ABC50 protein or a fragment thereof having protein synthesis increasing activity and/or eIF2 binding activity.

In a further embodiment, wherein the increase in expression and/or production is about 5% to about 10%, about 11% to about 20%, about 31% to about 40%, about 41% to about 50%, 51% to about 60%, 61% to about 70%, 71% to about 80%, about 81% to about 90%, about 91% to about 100%, about 150% to about 199%, about 200% to about 299%, about 300% to about 499%, or about 500% to about 1000%.

In an embodiment, the cell is a eukaryotic cell selected from a yeast, plant, worm, insect, avian, fish, reptile and mammalian cell. In another embodiment, the mammalian cell is a myeloma cell, a spleen cell, or a hybridoma cell. In yet a further embodiment, the mammalian cell is a leukemia cell, such as HL-60; or a hybridoma cell such as Sp2; or a chinese hamster ovary (CHO) cell.

The protein of interest or antibody of interest is, in an embodiment, a secreted protein, an intracellular protein, or a membrane protein.

In another embodiment, the protein of interest is an antibody or antibody fragment or derivative thereof. In an embodiment, the antibody is monoclonal, polyclonal, mammalian, murine, chimeric, humanized, primatized, primate, or human. In another embodiment, the antibody is a fragment or derivative thereof selected from antibody immunoglobulin light chain, immunoglobulin heavy chain, immunoglobulin light and heavy chains, Fab, F(ab')2, Fc, Fc-Fc fusion proteins, Fv, single chain Fv, single domain Fv, tetravalent single chain Fv, disulfide-linked Fv, domain deleted, minibody, diabody, a fusion protein of one of the above fragments with another peptide or protein or Fc-peptide fusion.

In an embodiment, the method further comprises isolating the protein of interest or the antibody of interest. Where, for example, the protein or antibody of interest is secreted, the method in an embodiment, further comprises isolating the secreted protein or secreted antibody of interest. Where, for example, the protein or antibody of interest is intracellular, the method further comprises in an embodiment, lysing the cell and isolating the intracellular protein or antibody of interest. In another embodiment, where the protein or antibody of interest is membrane or surface bound, the method in an embodiment, further comprises solubilizing the cell membrane and isolating the membrane protein or surface antibody of interest.

A further aspect provides a process for the production of a protein of interest comprising: culturing a cell, wherein the cell produces the protein of interest, increasing the expression or activity of a ABC50 protein or a fragment thereof having protein synthesis increasing activity and/or eIF2 binding activity, which enhances protein production; culturing the cell until the protein of interest accumulates, and isolating the protein of interest.

Another aspect provides a process for the production of a protein of interest comprising: culturing a cell wherein the cell comprises an expression vector that encodes the protein of interest and an expression vector that encodes a ABC50 protein under conditions that permit expression of the protein of interest and the ABC50 protein; culturing the cell until the protein of interest accumulates and isolating the protein of interest.

In an embodiment, the process provides for the production of a protein of interest, wherein the protein of interest is an antibody or antibody fragment.

Another aspect relates to a method of decreasing ABC50 levels in a cell comprising expressing an antisense agent that inhibits expression of ABC50 in the cell.

A further aspect provides a method of increasing sensitivity of a cell to ER stress agents comprising expressing an antisense agent that inhibits expression of ABC50 in the cell.

In an embodiment, the antisense agent is a siRNA, shRNA or an antisense oligonucleotide.

In a further embodiment, the shRNA comprises SEQ ID NO: 3 or 4.

In an embodiment, the ER stress agent is selected from EC, thapsigargin and tunicamycin.

Another aspect provides an isolated protein of interest produced according to a method described herein.

In an embodiment, the isolated protein produced according to a method described herein is an antibody or antibody fragment.

A further aspect provides an expression vector comprising a polynucleotide encoding an ABC50 polynucleotide and a polynucleotide comprising a protein of interest.

A further aspect relates to a cell comprising an expression vector described herein.

Yet a further aspect provides a cell comprising a heterologous ABC50 gene.

Another aspect relates to a composition comprising an isolated protein, vector or cell described herein.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the disclosure will now be discussed in relation to the drawings in which.

DETAILED DESCRIPTION OF THE DISCLOSURE

I. Definitions

Figure 1:
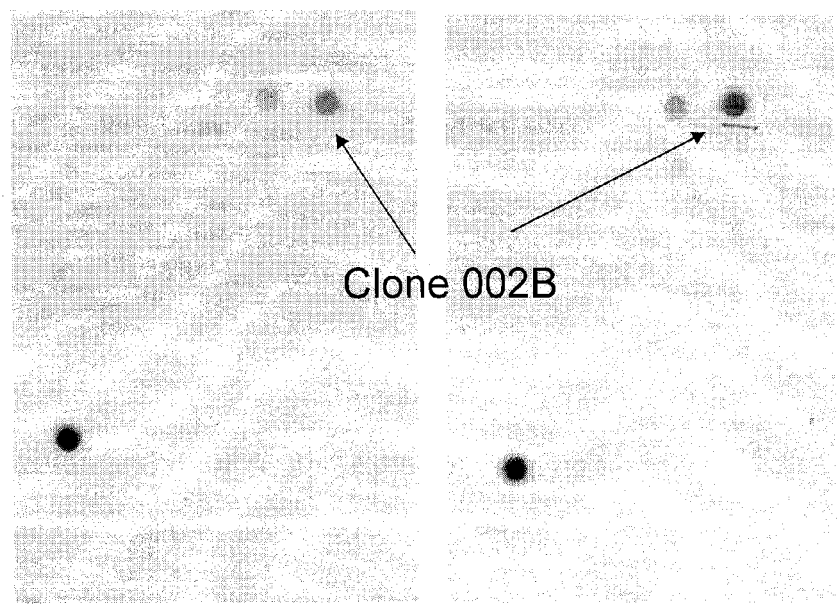
FIG. 1 Enhanced expression of ABC50 in Ec-resistant E2R2 cells. A: Reverse Northern analysis of genes identified by Differential Display as performed as described in Materials and Methods. Clone 002B, identified in this analysis as having increased expression was sequenced and found to be the ABC50 gene. B: Western blot of ABC50 in HL60 vs E2R2 cells. Actin expression was also evaluated to allow normalization between the two samples.

The term "ABC50" also known as ABCF1 refers to a member of the ATP Binding Cassette (ABC) family of proteins which lacks a transmembrane domain and includes for example human ABC50 with accession number AF027302 (SEQ ID NO:1)[1], mouse ABC50 (e.g. SEQ ID NO:5), rat ABC50 with accession number AF293383 (SEQ ID NO:2) (see for example, http://www.ncbi.nlm.nih.gov/sites/entrez?Db=gene&Cmd=ShowDetailView&Term ToSearch=85493&ordinalpos=3&itool=EntrezSystem2.PEntrez.Gene.Gene_Res ultsPanel.Gene_RVDocSum), as well as yeast homologs yeast elongation factor 3 (YEF3 Accession number NC_001144 geneID:850951) and GCN20 (Accession number NC_001138, geneID:850561). Other homologs are also contemplated including other mammalian homologs, including but not limited to mouse (SEQ ID NO:5; Accession number NM_013854), hamster, including Chinese hamster ABC50 and insect homologs. Species homologs can be identified for example using Blast basic local alignment search tool. In a preferred embodiment, the ABC50 is human ABC50.

The term "activity of an ABC50 protein" as used herein means a protein synthesis increasing activity of ABC50 protein (e.g. protein synthesis increasing activity) which may be mediated for example by increasing translation initiation complex formation between eIF2, GTP and/or Met-tRNA and/or by binding to eIF2.

The term " Econazole" or Ec refers to an antifungal agent of the imidazole cuss having IUPAC name 1-[2-[(4-chlorophenyl)methoxy]-2-(2,4-dichlorophenyl)ethyl]-1H-imidazole, formula $C_{18}H_{15}Cl_3N_2O$ and sold for example with brand names Spectazole™ (US), Ecostatin™ (Canada) and Pevaryl™ (Western Europe), Endix-G™ (Asia) Ecosone™ (Thailand).

The term "antibody" as used herein is intended to include monoclonal antibodies, polyclonal antibodies, and chimeric antibodies as well as surface immunoglobulins. The antibody is optionally mammalian, murine, chimeric, humanized, primatized, primate, or human and can be a single chain antibody or multichain antibody. The antibody may be from recombinant sources and/or produced in transgenic animals.

The term "antibody fragment" as used herein is intended to include Fab, Fab', F(ab')$_2$, scFv, dsFv, ds-scFv, dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques.

The term "cell" as used in methods for expressing a protein of interest or increasing expression of a protein of interest refers to an eukaryotic cell, for example a yeast cell, fungi, plant cell or mammalian cell, and also includes a fused cell such as hybridoma cell.

The term "a cell" includes a single cell as well as a plurality or population of cells. Contacting a cell or administering a composition to a cell includes in vivo, ex vivo and in vitro contact.

The term "protein" as used herein refers to a molecule comprised of amino acid residues, including for example single chain polypeptides, as well as a single chain of a multichain protein, multichain proteins such as traditional antibodies, recombinant polypeptides including for example fusion proteins, tagged proteins, mutant proteins and fragments, typically active fragments, of full length proteins. Protein and polypeptide are herein used interchangeably.

The term "protein of interest" refers to a protein being produced or whose expression is sought to be produced, by a method or process described herein, and includes for example but is not limited to therapeutic proteins such as cytokines, growth factors such as insulin, coagulation factors, vaccine subunits and therapeutic enzymes, and antibodies or fragments thereof, including recombinant or natural proteins.

The term "antibody of interest" refers to an antibody or antibody fragment being produced or whose expression is sought to be produced, by a method or process disclosed herein. For example, the antibody of interest can be an antibody produced by a hybridoma whose expression is sought to be increased by ABC50 overexpression.

The term "isolated protein" refers to a protein substantially free of cellular material or culture medium when produced by recombinant DNA techniques, or chemical precursors or other chemicals when chemically synthesized.

A "conservative amino acid substitution" as used herein, is one in which one amino acid residue is replaced with another amino acid residue without abolishing the protein's desired properties.

The phrase "conservative substitution" also includes the use of a chemically derivatized residue in place of a non-derivatized residue provided that such polypeptide displays the requisite activity.

In the context of a polypeptide, the term "derivative" as used herein refers to a polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as derivatives are those peptides which contain one or more naturally occurring amino acid derivatives of the twenty standard amino acids. For examples: 4-hydroxyproline may be substituted for proline; 5 hydroxylysine may be substituted for lysine; 3-methylhistidine may be substituted for histidine; homoserine may be substituted for serine; and ornithine may be substituted for lysine.

The term "polynucleotide" or alternatively "nucleic acid molecule" as used herein refers to a linked series of nucleoside or nucleotide monomers consisting of naturally occurring bases, sugars and intersugar (backbone) linkages, including for example cDNA, vectors and recombinant polynucleotides. The term also includes modified or substituted sequences comprising non-naturally occurring monomers or portions thereof, which function similarly. Such modified or substituted nucleic acid molecules may be preferred over naturally occurring forms because of properties such as enhanced cellular uptake, or increased stability in the presence of nucleases. The term also includes chimeric nucleic acid molecules that contain two or more chemically distinct regions. For example, chimeric nucleic acid molecules may contain at least one region of modified nucleotides that confer beneficial properties (e.g. increased nuclease resistance, increased uptake into cells), or two or more nucleic acid molecules described herein may be joined to form a chimeric nucleic acid molecule. The polynucleotides may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. Also, the term "nucleic acid" can be either double stranded or single stranded, and represents the sense or antisense strand. Further, the term "nucleic acid" includes the complementary nucleic acid sequences.

The term "isolated polynucleotide" and/or alternatively "isolated nucleic acid molecule" as used herein refers to a nucleic acid substantially free of cellular material or culture medium when produced by recombinant DNA techniques, or chemical precursors, or other chemicals when chemically synthesized. An isolated polynucleotide is also substantially free of residues which naturally flank the nucleic acid (i.e. residues located at the 5' and 3' ends of the nucleic acid) from which the nucleic acid is derived.

The term "complementary" in reference to a nucleic acid as used herein refers to the property of a double stranded nucleic acid including DNA and RNA and DNA:RNA hybrids to base-pair according to the standard Watson-Crick complementary rules, e.g. the capacity to hybridize to a particular nucleic acid segment under stringent conditions and/or to a nucleic acid single stand that has this property e.g. is complementary to a specific nucleic acid or portion thereof.

By "stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "control cell" as used herein refers a cell that does not have increased expression of an ABC50 protein or a fragment thereof having protein synthesis increasing activity and/or eIF2 binding activity.

The term "fragment thereof having protein synthesis increasing activity" in reference to ABC50 refers to a portion of ABC50 that retains the ability to increase protein synthesis for example, by at least 5%, at least 10% or more, for example by stimulating translation initiation complex formation between eIF2, GTP and/or Met-tRNA and/or binding to eIF2.

The term "fragment thereof having eIF2 binding activity" in relation to ABC50 refers to an active fragment of ABC50 that binds ABC50 and retains the ability to increase protein synthesis.

The terms "transformed with", "transfected with", "transformation" "transduced" and "transfection" are intended to encompass introduction of nucleic acid (e.g. a vector) into a cell by a variety of techniques known in the art. The term "transformed cell" as used herein is intended to also include cells capable of glycosylation that have been transformed with a recombinant expression vector disclosed herein.

The term "antisense agent" as used herein means a nucleotide polynucleotide that comprises a sequence of residues that is complementary to and binds a target RNA and decreases translation of its target RNA. For example, "antisense agents" include antisense oligonucleotides, as well as small interfering RNAs (siRNAs) and short hairpin RNAs (shRNAs). The nucleic acid can comprise DNA, RNA or a chemical analog, that binds to the messenger RNA produced by the target gene. Binding of the antisense agent presents translation and thereby inhibits or reduces target protein expression.

The term "siRNA" refers to a short inhibitory RNA duplex that can be used to silence gene expression of a specific gene by RNA interference (RNAi). A person skilled in the art will understand that RNAi technology uses paired oligonucleotides. Wherein a single strand sequence is identified by SEQ ID NO, a person skilled in the art using the rules of base pairing will readily determine the appropriate corresponding oligonucleotide.

The term "shRNA" refers to a short hairpin RNA. Typically shRNAs are approximately about 50, 60 or 70 nucleotides long, or any number in between, for example 54 nucleotides long and can give to miRNAs. The term "miRNA" refers to microRNAs which are single stranded RNAs, for example 22 nucleotides, that are processed from hairpin RNA precursors, for example about 50, 60 or 70 nucleotides long. miRNAs can inhibit gene expression through targeting homologous mRNAs. siRNAs and shRNAs activate a cellular degradation pathway directed at mRNAs corresponding to the siRNA or shRNA. Methods of designing specific siRNA and shRNA molecules and administering them are described herein and known to a person skilled in the art. For example siRNAs can comprise two 21-23 nucleotide strands forming a double stranded RNA molecule, wherein one strand is complementary to a target region in a gene of interest (e.g. comprises a sense strand homologous to the target mRNA). It is known in the art that efficient silencing is obtained with siRNA duplex complexes paired to have a two nucleotide 3' overhang. Adding two thymidine nucleotides is thought to add nuclease resistance. A person skilled in the art will recognize that other nucleotides can also be added.

The term "subject", as used herein includes all members of the animal kingdom, especially mammals, including human. The subject or patient is suitably a human.

II. Methods

ABC50 is a member of the ATP binding cassette protein family. Biochemically, ABC50 stimulates the formation of translation initiation complexes between eIF2, GTP and Met-tRNA implicating it in translation initiation and control for both Cap-dependent and -independent translation. Econazole (Ec) is an imidazole anti-fungal that induces endoplasmic reticulum (ER) stress in mammalian cells by promoting ER $Ca^{2+}$ depletion and sustained inhibition of protein synthesis. A previous characterization of HL60 cells selected for resistance to Ec found that the cells exhibited a phenotype of multi-drug resistance associated specifically with ER stress inducers. Differential Display Analysis of these cells identified ABC50 as a gene overexpressed in resistant cells. A similar selection process applied to sp2 cells also resulted in ER stress resistance and ABC50 overexpression. Knockdown of ABC50 in HL60 cells increased sensitivity to Ec in both parental HL60 and an Ec-resistant variant. ABC50 also altered sensitivity to the ER stress agents thapsigargin and tunicamycin. ABC50 knockdown increased ER $Ca^{2+}$ stores and thapsigargin-stimulated influx. Knockdown significantly suppressed protein synthesis levels while overexpression increased them. ABC50 overexpression also increased antibody production in the hybridoma GK1.5 indicating that ABC50 overexpression is useful for the overproduction of specific proteins. Taken together, these results indicate that ABC50 modulates sensitivity to Ec and other ER stress agents primarily through its effects on protein synthesis.

Accordingly, an aspect of the disclosure provides a method of producing a protein of interest comprising effecting expression of the protein of interest in a cell comprising an increased expression or activity of an ABC50 protein or a fragment thereof having protein synthesis increasing activity.

In an embodiment, the method comprises increasing the expression or activity of an ABC50 protein or a fragment thereof having protein synthesis increasing activity in a cell; and effecting the expression of the protein of interest.

In another embodiment, the method comprises effecting expression of the protein of interest in a cell comprising an increased expression or activity of an ABC50 protein or a fragment thereof having eIF2 binding activity.

In yet another embodiment, the method comprises increasing the expression or activity of an ABC50 protein or a fragment thereof having eiF2 binding activity; and effecting the expression of the protein of interest.

In an embodiment, the protein of interest is a heterologous protein.

Accordingly, in an embodiment, the method comprises producing a heterologous protein of interest comprises effecting expression of the protein of interest in a cell comprising an increased expression or activity of an ABC50 protein or a fragment thereof having protein synthesis increasing activity and/or eIF2 binding activity.

In another embodiment, the method comprises producing a heterologous protein of interest comprising increasing the expression or activity of an ABC50 protein or a fragment thereof having protein synthesis increasing activity and/or eIF2 binding activity; and effecting the expression of the protein of interest.

In an embodiment, the protein of interest is produced by a cell.

In an embodiment, the protein of interest is an antibody or antibody fragment.

Accordingly, another aspect includes a method of producing an antibody (e.g. an antibody of interest) or fragment thereof by a cell capable of expressing an antibody or fragment thereof comprising increasing the expression or activity of an ABC50 protein or a fragment thereof having protein synthesis increasing activity and/or eIF2 binding activity in the cell.

In an embodiment, the method comprises effecting expression of the antibody or fragment thereof in a cell comprising an increased expression or activity of an ABC50 protein or a fragment thereof having protein synthesis increasing activity and/or eIF2 binding activity.

In an embodiment, the expression or activity of ABC50 protein or a fragment thereof is increased by expressing a heterologous ABC50 polynucleotide encoding an ABC50 protein or a fragment thereof wherein the ABC50 polynucleotide is operatively linked to a promoter.

Effecting expression can for example be accomplished by culturing a cell under conditions suitable for protein expression, including for example culturing the cell at a growth permissive temperature, in a suitable culture medium, a sufficient time etc. that depend for example on the cell and desired expression level.

Another aspect relates to a method of increasing expression of a heterologous protein of interest by a cell expressing the protein of interest, comprising increasing the expression or activity of an ABC50 protein or a fragment thereof having protein synthesis increasing activity and/or eIF2 binding activity, wherein the increased expression or activity of the ABC50 protein or fragment increases the expression of the heterologous protein. In an embodiment, the method comprises introducing a polynucleotide encoding the heterologous protein and/or introducing a polynucleotide encoding the ABC50 protein or fragment into the cell, for example by transfection, transduction or infection.

In an embodiment, the expression or activity of ABC50 protein or a fragment thereof is increased and the expression of the protein of interest is effected by introducing a polynucleotide encoding the ABC50 protein or a fragment thereof, and a polynucleotide encoding the protein of interest, wherein the polynucleotides are operatively linked to one or more promoters and optionally comprised in one or more vectors.

A further aspect relates to a method of increasing expression of an antibody or fragment thereof in a cell expressing or capable of expressing the antibody or fragment of interest, comprising increasing the expression or activity of an ABC50 protein or a fragment thereof having protein synthesis increasing activity and/or eIF2 binding activity.

Cells capable of producing antibodies and/or fragments thereof may be prepared using techniques known in the art such as those described by Kohler and Milstein, Nature 256, 495 (1975) and in U.S. Pat. Nos. RE 32,011; 4,902,614; 4,543,439; and 4,411,993, which are incorporated herein by reference. (See also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Within the context of the disclosure, antibodies are understood to include monoclonal antibodies, polyclonal antibodies, antibody fragments (e.g., Fab, and $F(ab')_2$) and recombinantly produced binding partners.

For producing monoclonal antibodies the technique involves hyperimmunization of an appropriate donor with the immunogen, generally a mouse, and isolation of splenic antibody producing cells. These cells are fused to a cell, having immortality, such as a myeloma cell, to provide a fused cell hybrid which has immortality and secretes the required antibody. The cells are then cultured, in bulk, and the monoclonal antibodies harvested from the culture media for use.

For producing recombinant antibodies (see generally Huston et al., 1991; Johnson and Bird, 1991; Mernaugh and Mernaugh, 1995), messenger RNAs from antibody producing B-lymphocytes of animals, or hybridoma are reverse-transcribed to obtain complimentary DNAs (CDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

As disclosed herein, ABC50 expression and/or activity can be increased by selecting for Econazole resistant cells. Accordingly, in another embodiment, the expression or activity of ABC50 protein or a fragment thereof is increased by contacting the cell with increasing concentrations of Econazole (Ec), and detecting increased expression or activity of ABC50 protein. For example, Ec resistance can be induced by contacting the cell with a sufficient concentration of Econazole (Ec) to increase expression or activity of an ABC50 protein and selecting cells that maintain increased ABC50 expression and/or activity.

ABC50 expression and/or activity can be increased by introducing a heterologous ABC50 polynucleotide into a cell that is expressed. Accordingly in another embodiment, the expression or activity of ABC50 protein or a fragment thereof is increased by introducing a heterologous ABC50 polynucleotide encoding ABC50 protein or a fragment thereof operatively linked to a promoter, into the cell.

In another embodiment, the cell already comprises a heterologous polynucleotide encoding the protein of interest operatively linked to a promoter.

In a further embodiment, polynucleotides encoding ABC50 and the protein or interest are cointroduced into a cell. Accordingly, in an embodiment, the expression or activity of ABC50 protein or a fragment thereof is increased and the expression of the protein of interest is effected by introducing a vector comprising a polynucleotide encoding ABC50 protein or a fragment thereof, and a heterologous polynucleotide of the protein of interest, wherein the polynucleotides are operatively linked to one or more promoters. For example, expression of two polynucleotides can be achieved using an internal ribosomal entry site (IRES).

The polynucleotides may be incorporated in a known manner into an appropriate expression vector, which ensures good expression of the polypeptides. Various constructs can be used. For example retroviral constructs such as lentiviral constructs are useful for expressing physiological levels of protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The disclosure therefore includes use of a recombinant expression vector containing a polynucleotide molecule disclosed herein, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors may also contain a selectable marker gene which facilitates the selection of host cells transformed or transfected with a recombinant molecule disclosed herein. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of the recombinant expression vectors disclosed herein and in particular to determine the effect of a mutation on expression and phenotype. It will be appreciated that selectable markers can be introduced on a separate vector from the nucleic acid of interest.

Other selectable markers include for example, dihydrofolate reductase (DHFR) and glutamine synthetase (GS) for examples for use in CHO of NS0 cells, respectively. Selection occurs in the absence of the metabolites e.g. glycine, hypoxanthine and thymidine for DHFR and glutamine for GS. Cells surviving selection comprise one or more copies of the transfected plasmid in the cell's genome. Further amplification of the copy number of the integrated DNA can be achieved by exposure of the selected cells to increasing levels of methotrexate (MTX) or methioninen sulphoximine (MSX) respectively [8]. The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Transcription of the protein of interest and/or ABC50 can be under the control of an inducible expression system. Accordingly, in an embodiment, effecting the expression of the protein of interest and/or ABC50 comprises contacting the cell with an inducer that induces expression of the protein of interest and/or ABC50. Examples of inducible expression systems include the Tet-on or Tet-off inducible expression systems.

Recombinant expression vectors can be introduced into host cells to produce a recombinant cell by one of many possible techniques known in the art. For example, a polynucleotide can be introduced by transforming a cell (e.g. electroporating a prokaryotic cell), transfecting a cell (e.g. using lipofectin) or transducing a cell (e.g. using a retrovirus). Prokaryotic cells can be transformed with a polynucleotide by, for example, electroporation or calcium-chloride mediated transformation. For example, polynucleotide can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

In other embodiments, the cells are optionally transduced with retroviral constructs that drive expression of ABC50 and/or the protein or antibody of interest. Methods of transducing cells are well known in the art. Methods of transducing/infecting cells with lentiviral vectors are also described herein.

Different ABC50 proteins can be used with the methods disclosed herein. For example, human ABC50, rat ABC50 and/or yeast ABC50 homolog can be used. Also, the ABC50 protein employed is optionally, the same species as the cell in which it is expressed (e.g. human ABC50, and human cell). Alternatively, the ABC50 protein employed is from a different species from the cell (e.g. human ABC50, yeast cell). Nucleic acids encoding human ABC50 were utilized in transfection/transduction experiments described herein and mouse Sp2 cells were treated with Ec selection. Ec selection of mouse Sp2 resulted in increased ABC50 expression as described indicating that different ABC50 molecules (e.g. proteins and nucleic acids) are useful in the methods of the disclosure. *Mus musculus* sequence is for example 88% identical and 91% similar to human ABC50 according to a BLAST comparison.

In an embodiment, the ABC50 protein comprises SEQ ID NO: 1, 2 or 5; or a protein with at least 85%, 88%, 90%, 95%, 99% or 99.5% sequence identity with SEQ ID NO:1, 2 or 5.

In an embodiment, the ABC50 polynucleotide comprises SEQ ID NO:6, 7 or 8; or a polynucleotide with at least 85%, 88%, 90%, 95%, 99% or 99.5% sequence identity with SEQ ID NO:6, 7 or 8.

In an embodiment, the method results in increased specific cellular expression and/or production of the protein of interest in comparison to a control cell expressing the protein of interest wherein the control cell does not have increased expression (e.g. has wildtype levels) of an ABC50 protein or a fragment thereof having protein synthesis increasing activity and/or eIF2 binding activity.

In an embodiment, the method results in increased specific cellular expression and/or production of the antibody of interest in comparison to a control cell expressing the antibody of interest wherein the control cell does not have increased expression of an ABC50 protein or a fragment thereof having protein synthesis inducing activity and/or eIF2 binding activity.

In an embodiment, the increase in expression and/or production of the protein or antibody of interest is about 5% to about 10%, about 11% to about 20%, about 31% to about 40%, about 41% to about 50%, 51% to about 60%, 61% to about 70%, 71% to about 80%, about 81% to about 90%, about 91% to about 100%, about 150% to about 199%, about 200% to about 299%, about 300% to about 499%, or about 500% to about 1000%. In an embodiment, the increase is at least 5%. In another embodiment, the increase is at least 10%.

The level of ABC50 protein and/or fragment expression and/or activity is increased for example by an amount sufficient to increase expression of the protein of interest. The increase in ABC50 protein or active fragment thereof expression or activity is in an embodiment, about 5% to about 10%, about 11% to about 20%, about 31% to about 40%, about 41% to about 50%, 51% to about 60%, 61% to about 70%, 71% to about 80%, about 81% to about 90%, about 91% to about 100%, about 150% to about 199%, about 200% to about 299%, about 300% to about 499%, or about 500% to about 1000%. In an embodiment, the increase in ABC50 protein or active fragment thereof expression or activity is at least 10%, at least 20%, at least 30% at least 40%, at least 50%, at least 60%, at least 65% or at least 70%.

Suitable host cells include a wide variety of prokaryotic and eukaryotic host cells. For example, the polynucleotides and constructs that encode proteins or antibodies of interest may be expressed in bacterial cells such as *E. coli*. Other suitable host cells can be found in Goeddel (Goeddel, Gene Expression Technology Methods in Enzymology 185, Academic Press, San Diego, Calif. 1990).

More particularly, bacterial host cells suitable for carrying out the present disclosure include *E. coli, B. subtilis, Salmonella typhimurium*, and various species within the genus *Pseudomonas, Streptomyces*, and *Staphylococcus*, as well as many other bacterial species well known to one of ordinary skill in the art. Suitable bacterial vectors preferably comprise a promoter which functions in the host cell, one or more selectable phenotypic markers, and a bacterial origin of replication. Representative promoters include the β-lactamase (penicillinase) and lactose promoter system (see Chang et al. Chang et al., *Nature* 275:615 (1978)), the trp promoter (Nichols and Yanofsky, *Meth. in Enzymology* 101:155, 1983) and the tac promoter (Russell et al., *Gene* 20: 231, 1982). Representative selectable markers include various antibiotic resistance markers such as the kanamycin or ampicillin resistance genes. Suitable expression vectors include but are not limited to bacteriophages such as lambda derivatives or plasmids such as pBR322 (see Bolivar et al. (Bolivar et al., *Gene* 2:9 S, 1977)), the pUC plasmids pUC18, pUC19, pUC118, pUC119 (see Messing (Messing, *Meth in Enzymology* 101: 20-77, 1983) and Vieira and Messing (Vieira and Messing, *Gene* 19:259-268 (1982)), and pNH8A, pNH16a, pNH18a, and Bluescript M13 (Stratagene, La Jolla, Calif.). Typical fusion expression vectors which may be used are discussed above, e.g. pGEX (Amrad Corp., Melbourne, Australia), pMAL (New England Biolabs, Beverly, Mass.) and pRIT5 (Pharmacia, Piscataway, N.J.). Examples of inducible nonfusion expression vectors include pTrc (Amann et al., *Gene* 69:301-315 (1988)) and pET 11d (Studier et al., Gene Expression Technology: Methods in Enzymology 185, Academic Press, San Diego, Calif., 60-89 (1990)).

The protein of interest can be expressed in any eukaryotic cell, including but not limited to insect cells (using baculovirus), yeast cells or mammalian cells. Yeast and fungi host cells suitable for use include, but are not limited to *Saccharomyces cerevisiae, Schizosaccharomyces pombe*, the genera *Pichia* or *Kluyveromyces* and various species of the genus *Aspergillus*. Examples of vectors for expression in yeast *S. cerivisiae* include pYepSec1 (Baldari et al., *Embo J.* 6:229-234 (1987)), pMFa (Kurjan and Herskowitz, *Cell* 30:933-943 (1982)), pJRY88 (Schultz et al., *Gene* 54:113-123 (1987)), and pYES2 (Invitrogen Corporation, San Diego, Calif.). Protocols for the transformation of yeast and fungi are well known to those of ordinary skill in the art (see Hinnen et al. (Hinnen et al., *Proc. Natl. Acad. Sci. USA* 75:1929 (1978)); Itoh et al. (Itoh et al., *J. Bacteriology* 153:163 (1983)), and Cullen et al. (Cullen et al. *Bio/Technology* 5:369 (1987)).

Mammalian cells suitable for use include, among others: HL60, COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (36) and pMT2PC (Kaufman et al., *EMBO J.* 6:187-195 (1987)).

Given the teachings provided herein, promoters, terminators, and methods for introducing expression vectors of an appropriate type into plant, avian, and insect cells may also be readily accomplished. For example, within one embodiment, the polypeptides disclosed herein may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034).

Suitable insect cells include cells and cell lines from *Bombyx, Trichoplusia* or *Spodotera* species. Baculovirus vectors available for expression of proteins in cultured insect cells (SF 9 cells) include the pAc series (Smith et al., Mol. Cell.

Biol. 3:2156-2165 (1983)) and the pVL series (Luckow, V. A., and Summers, M.D., Virology 170:31-39 (1989).

Alternatively, proteins and antibodies of interest may also be expressed in non-human transgenic animals such as rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866).

Accordingly, in an embodiment protein of interest is expressed by a eukaryotic cell. In an embodiment, the eukaryotic cell is selected from a yeast, plant, worm, insect, avian, fish, reptile and mammalian cell. In an embodiment, the cell is a mammalian cell. In another embodiment, the mammalian cell is a myeloma cell, a spleen cell, or a hybridoma cell producing a specific antibody. In a further embodiment, the cell is a Sp2, a NS0, a CHO, a Per.c6, a L cell. In a further embodiment, the mammalian cell is a leukemia cell, such as HL-60. In the case of increasing expression of an antibody or fragment thereof, the ABC50 protein or activity level can be increased in one or both the hybridoma fusion partners and/or in the fused hybridoma cell. In another embodiment, the hybridoma cell is GK1.5. In a further embodiment, the cell is an Ec resistant cell. In another embodiment, the cell is an Ec resistant Sp2 cell, NS0, CHO, Per.c6, or L cell. In an embodiment, the cell is a suspension culture adapted CHO cell. In a further embodiment, the Ec resistant Sp2 cell is fused to an antibody producing spleen cell. In an embodiment, the cell is not a HEK-293 cell.

A person skilled in the art will recognize that hybridomas expressing different monoclonal antibodies can be used and/or made using the methods of the disclosure.

In an embodiment, the protein of interest or antibody of interest is a secreted protein, an intracellular protein, or a membrane protein. In an embodiment, the protein of interest is a secreted protein.

Examples are provided for example in Hacker et al BioPharm International incorporated herein by reference [8]. In an embodiment, the protein of interest is an antibody or antibody fragment or derivative thereof. For example, yeast cells and plant cells have been engineered to produce recombinant proteins such as recombinant monoclonal antibodies (for example see Nature Protocols 1, 755-768 (2006); Hiatt A, Ma J, Lehner T and Mostov K. Method for producing immunoglobulins containing protection proteins in plants and their use 2004 U.S. Pat. No. 6,303,341; Hein M, Hiatt A and Ma J. Transgenic crops expressing assembled secretory antibodies 2006 U.S. Pat. No. 6,995,014; Ma J K, Lehner T, Stabila P, Fux Cl and Hiatt A. Assembly of monoclonal antibodies with IgG1 and IgA heavy chain domains in transgenic tobacco plants. *Eur J. Immunol.* 1994 January; 24(1):131-8; Ma J K, Hiatt A, Hein M, Vine N D, Wang F, Stabila P, van Dolleweerd C, Mostov K and Lehner T. Generation and assembly of secretory antibodies in plants. *Science* 1995, 268(5211), 716-9; Ma J K, Hikmat B Y, Wycoff K, Vine N D, Chargelegue D, Yu L, Hein M B and Lehner T. Characterization of a recombinant plant monoclonal secretory antibody and preventive immunotherapy in humans. *Nat. Med.* 1998, 4(5), 601-6, each of which are herein incorporated by reference).

In an embodiment, the antibody is monoclonal, polyclonal, mammalian, murine, chimeric, humanized, primatized, primate, or human.

In an embodiment, the antibody is a fragment or derivative thereof selected from antibody immunoglobulin light chain, immunoglobulin heavy chain, immunoglobulin light and heavy chains, Fab, F(ab')2, Fc, Fc-Fc fusion proteins, Fv, single chain Fv, single domain Fv, tetravalent single chain Fv, disulfide-linked Fv, domain deleted, minibody, diabody, a fusion protein of one of the above fragments with another peptide or protein or Fc-peptide fusion.

The antibody is in an embodiment, an IgG, IgM, IgA, IgD or IgE antibody. In a preferred embodiment, the antibody is an IgG antibody. In a further embodiment, the antibody is IgG such as IgG1, IgG2, IgG3 or IgG4.

In another embodiment, the method further comprises isolating the protein of interest or the antibody of interest.

A variety of methods are known for isolating proteins and antibodies. The method of isolation chosen can be affected by whether the protein is secreted, membrane bound or intracellular. In an embodiment, wherein the protein or antibody of interest is secreted, for example into a culture medium, the method further comprising isolating the secreted protein or secreted antibody of interest, for example from the culture supernatant. For example, the culture supernatant is collected and optionally fractionated. In another embodiment, wherein the protein or antibody of interest is intracellular, the method further comprising pelleting and/or lysing the cell and isolating the intracellular protein or antibody of interest. In an embodiment, wherein the protein or antibody of interest is membrane or surface bound, the method further comprising solubilizing the cell membrane and isolating the membrane protein or surface antibody of interest. For example for antibodies, binding to antigen can be used to isolate antibodies. The most common method is protein A columns. Other methods of purification include ammonium sulphate precipitation, ion exchange, gel filtration and hydrophobic interaction columns.

The disclosure also provides a process comprising the methods or aspects described herein. Accordingly, another aspect provides a process for the production of a protein of interest comprising: culturing a cell under suitable culture conditions (e.g. temperature, ambient environment, culture medium, length of time etc), wherein the cell produces the protein or antibody of interest, increasing the expression or activity of a ABC50 protein or a fragment thereof having eIF2 binding activity sufficiently to enhance protein production; culturing the cell until the protein of interest accumulates, and isolating the protein of interest. The protein of interest is an embodiment, a heterologous protein.

Another aspect provides a process for the production of a protein of interest comprising: culturing a cell, wherein the cell comprises an expression vector that encodes the protein of interest and an expression vector that encodes a ABC50 protein, under suitable culture conditions (e.g. temperature, ambient environment, culture medium etc) that permit expression of the protein of interest and the ABC50 protein; culturing the cell until the protein of interest accumulates and isolating the protein of interest.

As mentioned previously, in an embodiment protein of interest is an antibody or fragment thereof.

In an embodiment, the cell is a hybridoma cell and/or a hybridoma fusion partner.

It is also disclosed herein that decreasing ABC50 levels can be useful. Accordingly, another aspect provides a method of decreasing ABC50 levels in a cell comprising expressing an antisense agent that inhibits expression of ABC50 in the cell.

For example, decreasing ABC50 levels increases sensitivity to ER stress agents. Accordingly, another aspect provides a method of increasing sensitivity of a cell to ER stress agents comprising expressing an antisense agent that inhibits expression of ABC50 in the cell.

In an embodiment, the antisense agent is a siRNA, shRNA or an antisense oligonucleotide. In an embodiment, the antisense agent comprises SEQ ID NO:3. In another embodiment, the antisense agent comprises SEQ ID NO:4. The shRNA is in an embodiment, comprised in a lentiviral vector or virus.

In an embodiment, the shRNA comprises SEQ ID NO: 3 or 4.

In an embodiment, the decrease in ABC50 level is about 10% to about 20%, about 21% to about 30%, about 31% to about 40%, about 41% to about 50%, 51% to about 60%, 61% to about 70%, 71% to about 80%, 81% to about 90% or about 91% to about 100%.

In another embodiment, the ER stress agent is selected from EC, thapsigargin and tunicamycin.

III. Proteins and Expression Constructs

The disclosure also provides for isolated proteins produced using a method or process described herein. Accordingly, an aspect provides an isolated protein of interest produced according to the method or process described herein.

The isolated protein is in an embodiment, an antibody or antibody fragment.

The disclosure also provides in another embodiment, an expression vector comprising a polynucleotide encoding an ABC50 polynucleotide and optionally a polynucleotide comprising a protein of interest. Suitable vectors are described for example above and in the examples below.

In an embodiment, the vector comprises a polynucleotide encoding an ABC50 polynucleotide and optionally a polynucleotide encoding a protein of interest, wherein the polynucleotide(s) is/are operably linked to one or more promoters. In an embodiment, the vector is a retroviral vector, optionally a lentiviral vector.

IV. Cells

Another aspect provides a recombinant and/or isolated cell. In an embodiment, the recombinant cell comprises a vector described herein. In another embodiment, the recombinant cell comprises a heterologous ABC50 gene. In yet a further embodiment, the cell comprises an EC resistant cell comprising increased ABC50 expression or activity.

In and embodiment, the cell comprises a heterologous ABC50 polynucleotide operably linked to a promoter or an Ec resistant cell wherein the Ec resistant cell has increased ABC50 protein levels or activity compared to a non-Ec resistant control cell, wherein the cell is suitable and/or adapted for expression of a protein of interest. For example, a hybridoma fusion partner cell is such a suitable cell as a hybridoma fusion partner cell expressing the increased ABC50 is useful for fusing with any antibody cell to produce a hybridoma with increased antibody production compared to a hybridoma cell not comprising increased ABC50 expression. As another example, any eukaryotic cell that is transfectable, transduceable or infectable and that is useful for expressing proteins, for example in large amounts, is also a suitable cell.

In an embodiment, the EC resistant cell is an Ec resistant SP2 cell, CHO cell, NS0 cell, a Per.c6 or L cell.

Suitable host cells are described above. In an embodiment, the cell is selected from a yeast, plant, worm, insect, avian, fish, reptile, mammalian, hybridoma, a myeloma cell or a spleen cell.

A further aspect provides a system for increasing expression of a protein of interest, the system comprising a cell comprising increased expression or activity of ABC50. For example, the cell can be a frozen cell or a lyophilized cell. In an embodiment the system further comprises an expression vector in which can be introduced a polynucleotide encoding a protein of interest. In an embodiment, the ABC50 expression or activity increase results from introduction of a heterologous polynucleotide encoding ABC50. In another embodiment, the ABC50 expression or activity increase results from selection with Ec. In a further embodiment, the system comprises Ec such as in a form suitable for administration to a cell to maintain selective pressure, for example as a stock solution in DMSO for administering to cells at a concentration of for example 5, 10, 15, 20 or 25 microM.

V. Compositions

In another aspect, the isolated protein, vector or recombinant cell is comprised in a composition. In yet a further embodiment, the composition comprises a polynucleotide comprising SEQ ID NO:3. In another embodiment, the composition comprises a polynucleotide comprising SEQ ID NO:4. In a further embodiment, the composition comprises a carrier. In another embodiment, the carrier is a pharmaceutically acceptable carrier. In a further aspect, the composition is for decreasing the level of ABC50.

The following non-limiting examples are illustrative of the present disclosure:

EXAMPLES

Example 1

Recently, the inventor showed that transformation by the c-myc oncogene sensitizes cells to Ec by enhancing ROS generation at the mitochondria[9] providing at least one mechanism by which cancer cells exhibit sensitivity to Ec.

Previously, the inventor generated and characterized variants of HL60 cells that were resistant to Ec [10]. Although selected for resistance to Ec, the cells also displayed resistance to other ER stress agents including thapsigargin, tunicamycin, DTT and cycloheximide, thus defining a novel phenotype of multi-drug resistance associated with ER stress. Resistance was found to be associated with increased store-operated $Ca^{2+}$ influx capability and sustained protein synthesis after exposure to Ec. Microarray analysis of a resistant clone revealed increased expression of ribosomal protein genes. Biochemical analysis showed that this increased gene expression was associated with increased ribosomal content. Ribosome inactivating toxins partially reversed resistance to ER stress suggesting that the increased ribosomal content and function contributed to resistance.

To further identify genes associated with resistance and sensitivity to Ec, the inventor performed differential display analysis[11] comparing the Ec-resistant cell line E2R2 with parental HL60 cells. This analysis identified ABC50 as a gene overexpressed in Ec-resistant cells. ABC50 contributes to Ec-resistance.

Results

Differential Display of Ec-Resistant Vs Sensitive HL60 cells.

In order to identify additional genes associated with Ec resistance, Differential Display analysis was performed[11] comparing Ec-resistant E2R2 cells with parental HL60 cells. This analysis identified approximately 200 gene fragments that appeared to be overexpressed in E2R2 cells compared to Wild Type. These gene fragments were cloned and Reverse Northern analysis was employed to confirm differential expression. 50 of the 200 genes had expression levels above the detection limit of the Reverse Northern. Of the 50, 15 genes were confirmed to be differentially expressed. Sequence analysis identified these genes as follows: Two of the 15 encoded ribosomal protein genes, three encoded Alu-containing sequences, two were mitochondrial genes and one gene encoded the integrin CD11a. Two genes were identified that are classified as TNFα inducible. These were HLA gene (Bw-62), and ABC50 (NM_001090; aka ABCF1), a member of the ATP binding cassette family (FIG. 1A). Two additional genes of unknown function with no known homology or similarity to any other gene (AC114546, AC012358) were identified. One codes for hypothetical protein FLJ12363 (XP_043979) with no known function. The final gene identified in this screen was polyubiquitin C (AB009010). The protein and nucleic acid sequence of the aforementioned genes referred to by accession number, are herein specifically incorporated by reference.

ABC50 Protein Levels in E2R2 Cells.

ABC50 was investigated. It was first confirmed that ABC50 was overexpressed in E2R2 cells. As shown in FIG. 1B, increased levels of ABC50 protein were detected in E2R2 cells compared to HL60 cells. Densitometric analysis of Western blots indicated a 65% increased expression (relative to actin) of ABC50 in E2R2 compared to HL60 cells.

ABC50 Knockdown (KD) in E2R2 Cells.

Figure 2:
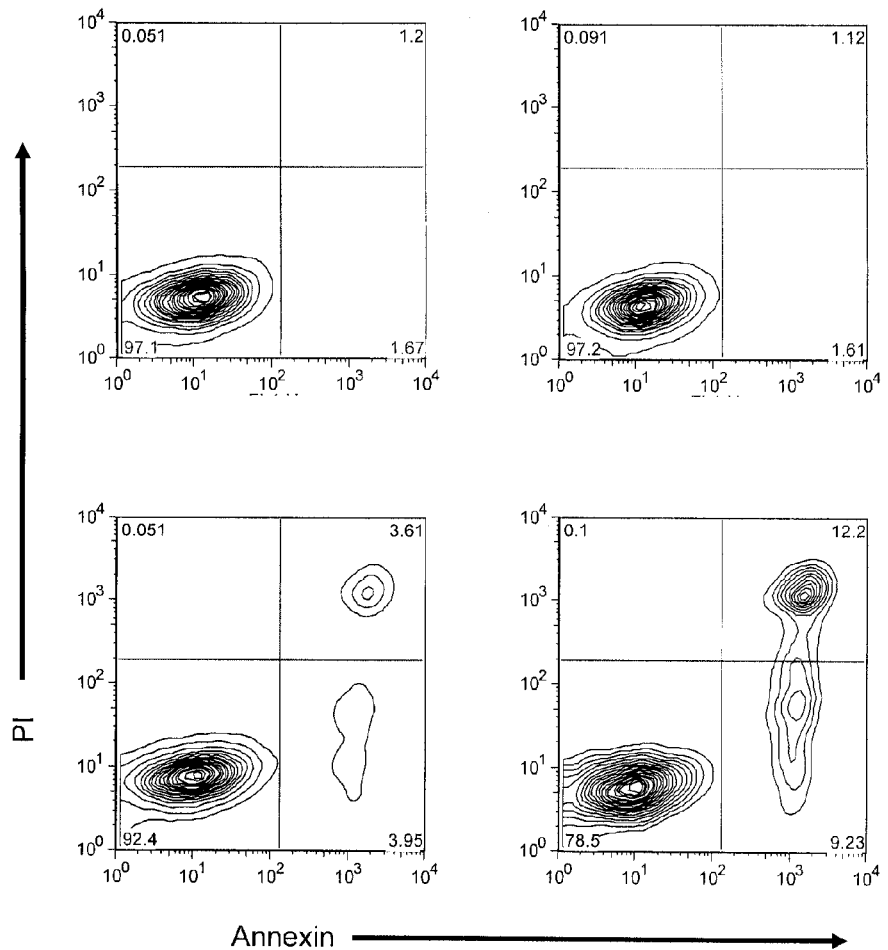
FIG. 2 ABC50 knockdown partially reverses resistance to Ec in E2R2 cells. A: Western blot of ABC50 expression in E2R2 cells infected with vector control or ABC50 shRNA. B: Apoptosis induction by Ec in E2R2 vector control and ABC50 knockdown cells. Cells were exposed to 15 µM Ec for 2 hours followed by overnight recovery as described in Materials and Methods. The following day, cells were stained with PI and AnnexinV and analysed by flow cytometry. AnnexinV positive, PI negative cells represent early apoptotic cells, AnnexinV positive, PI positive cells represent late apoptotic or necrotic cells.

The association of ABC50 with the Ec-resistance phenotype of E2R2 cells was further investigated by knocking down its expression in these cells. The cells were infected with a lentiviral vector expressing shRNA specific for ABC50 and sorted based on GFP expression. As shown in FIG. 2A, ABC50 knockdown was successful in these cells (36% relative decrease compared to vector control). Furthermore, as shown in FIG. 2B, ABC50 knockdown in E2R2 cells partially reversed their resistance to Ec (21.4% combined early and late apoptosis compared to 7.6% combined early and late apoptosis in the control cells), consistent with a role for ABC50 in the Ec resistance phenotype.

ABC50 Knockdown in HL60 Cells Increases Sensitivity to ER Stress Agents.

Figure 3:
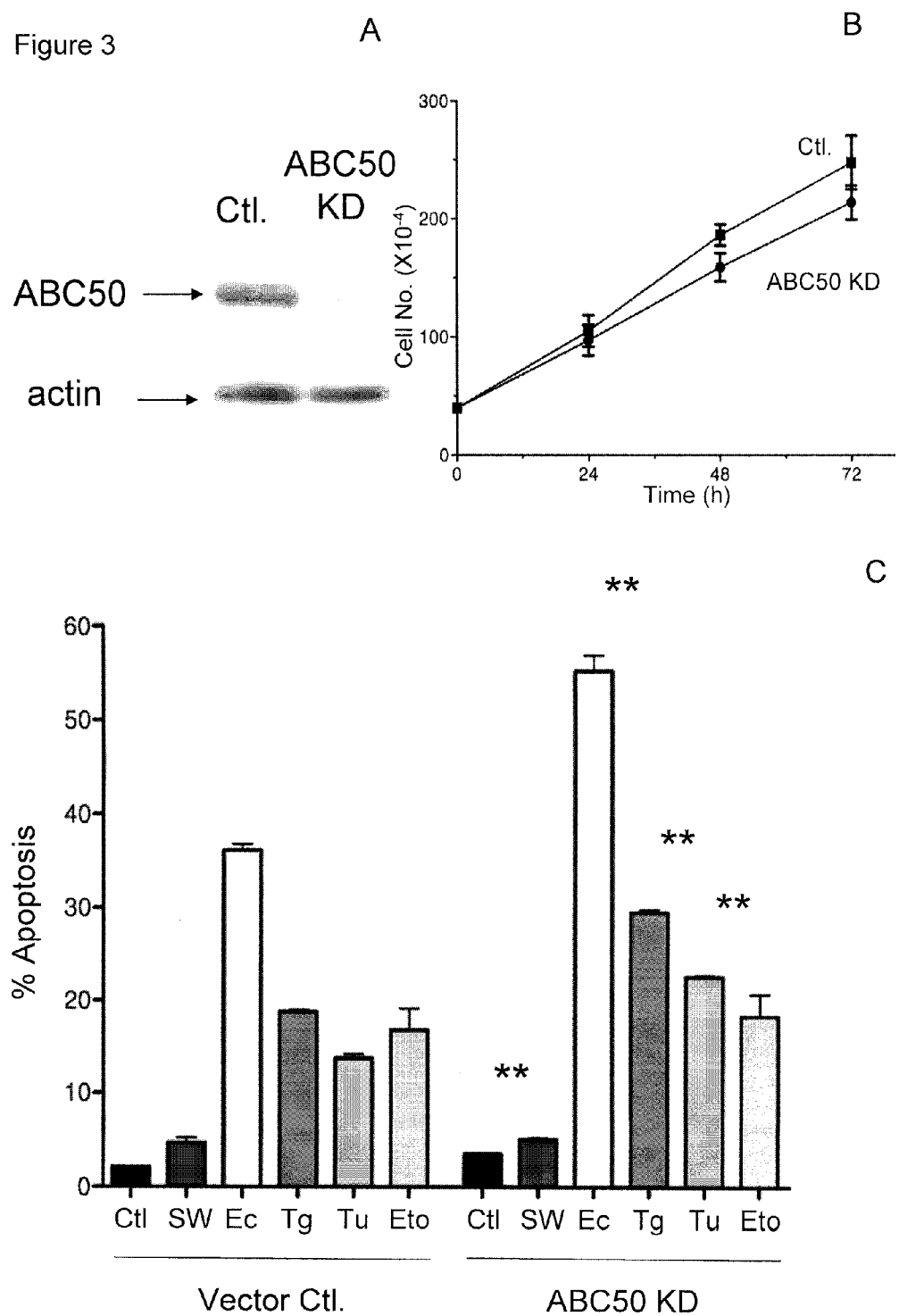
FIG. 3 ABC50 knockdown alters growth rate and sensitivity to Ec in HL60 cells. A: Western blot of ABC50 expression in HL60 cells infected with vector control or ABC50 shRNA. B: Cell growth kinetics of control and ABC50 knocked-down cells. Values are means and standard errors determined from triplicate cultures and is representative measurement from a series of three independent experiments. ***indicates p<0.001 at 48 hours for ABC50 KD cells vs control. C: Apoptosis induction by serum withdrawal (SW), Ec, Tg, Tu and etoposide (Eto) in HL60 vector control and ABC50 knockdown cells. Cells were exposed to 15 µM Ec for 2 hours followed by overnight recovery as described in Materials and Methods. Cells were incubated overnight in the absence of serum, 200 nM Tg, 1 µM Tu or 5 µM etoposide. The following day, cells were stained with PI and AnnexinV and analysed by flow cytometry. AnnexinV positive, PI negative cells represent early apoptotic cells, AnnexinV positive, PI positive cells represent late apoptotic or necrotic cells. Plotted is early and late apoptotic cells combined. $*p<0.05$, $**p<0.01$ comparing knockdown or overexpressing cells to their vector control.

To investigate further the consequences of manipulating ABC50 levels in cells, parental HL60 cells were infected with the lentiviral vector expressing shRNA specific for ABC50 and sorted infected cells based on GFP expression. As shown in FIG. 3A, the shRNA knocked down expression of ABC50 by 89% compared to vector control. Light microscopic observation revealed that the cells had no obvious morphological differences. It was also found that the knocked-down cells grew at a rate that was not significantly different from the control cells (FIG. 3B).

The effect of ABC50 knockdown on sensitivity to Ec and other apoptosis-inducing agents was next investigated. Tg is a classic inducer of ER stress and HL60 cells selected for resistance to Ec were also found to be resistant to Tg. Sensitivity to Tunicamycin (Tu), an inhibitor of protein glycosylation and another classic inducer of ER stress was also tested. As shown in FIG. 3C, ABC50 knockdown significantly increased the sensitivity of HL60 cells to Ec, Tg and Tu. In contrast, ABC50 KD did not affect sensitivity to serum withdrawal or the topoisomerase inhibitor etoposide. This observation suggests that ABC50 knockdown specifically increases sensitivity to ER stress-inducing agents.

ABC50 Overexpression in HL60 Cells Decreases Sensitivity to ER Stress Agents.

Figure 4:
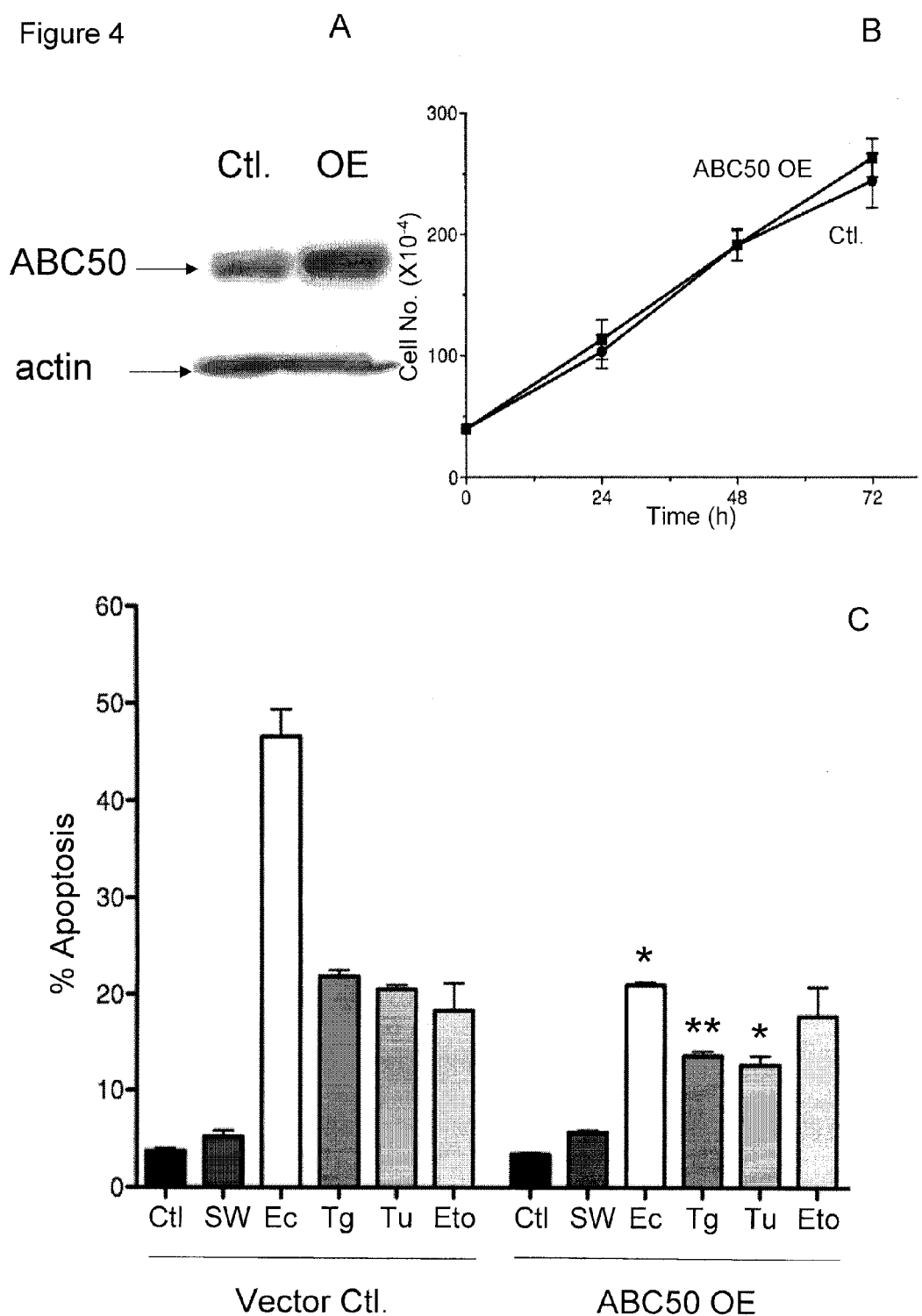
FIG. 4 Effect of ABC50 overexpression on growth rate and sensitivity to ER stress agents in HL60 cells. A: Western blot of ABC50 expression in HL60 cells infected with vector control or ABC50 OE vector. B: Cell growth kinetics of control and ABC50 overexpressing cells. Values are means and standard errors determined from triplicate cultures and is representative measurement from a series of three independent experiments. C: Apoptosis induction by serum withdrawal (SW), Ec, Tg, Tu and etoposide (Eto) in HL60 vector control and ABC50 overexpressing cells. Cells were exposed to 15 µM Ec for 2 hours followed by overnight recovery as described in Materials and Methods. Cells were incubated overnight in the absence of serum, 200 nM Tg, 1 µM Tu or 5 µM etoposide. The following day, cells were stained with PI and AnnexinV and analysed by flow cytometry. AnnexinV positive, PI negative cells represent early apoptotic cells, AnnexinV positive, PI positive cells represent late apoptotic or necrotic cells. Plotted is early and late apoptotic cells combined. $*p<0.05$, $**p<0.01$ comparing knockdown or overexpressing cells to their vector control.

The observation of increased ABC50 expression in the Ec-resistant E2R2 cells suggested that overexpression of the gene might promote resistance. To investigate this possibility, HL60 cells were infected with a lentiviral vector expressing the full ABC50 coding sequence, infected cells were sorted as above using the GFP marker, and the cell phenotype was analysed. As shown in FIG. 4A, infection with the ABC50 lentiviral vector significantly increased expression of the protein (42% relative increase compared to vector control). Cell growth properties were measured and it was found that the ABC50 overexpressing cells had no significant differences in growth kinetics compared to control HL60 cells infected with vector alone (FIG. 4B). However as shown in FIG. 4C, ABC50 overexpressing cells displayed decreased sensitivity to the ER stress agents Ec, Tg and Tu whereas their sensitivity to serum withdrawal or etoposide was unchanged compared to control cells. Taken together, these results demonstrate that ABC50 expression levels specifically affect sensitivity to ER stress.

ER $Ca^{2+}$ Content and Influx in ABC50 Knockdown and Overexpressing

Figure 5:
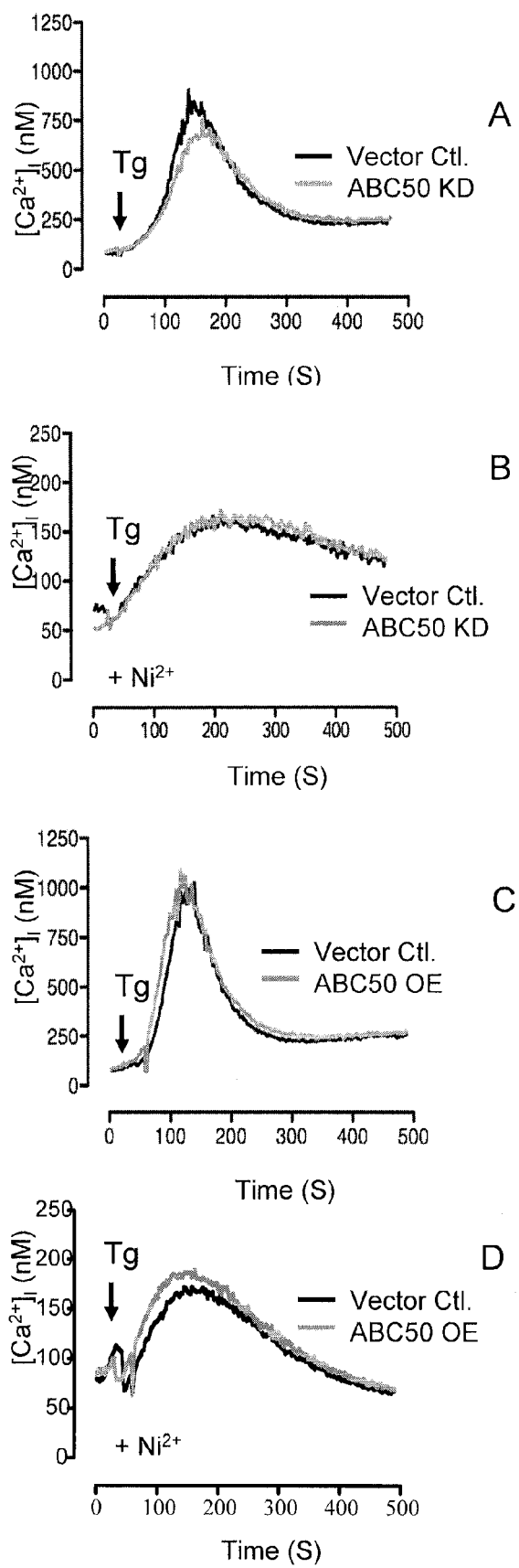
FIG. 5 Effect of ABC50 knockdown or overexpression on ER $Ca^{2+}$ stores and influx in HL60 cells. HL60 cells were loaded with the $Ca^{2+}$-sensitive dye Indo-1 as described in Materials and Methods. Cells were incubated (or not) in 5 mM $Ni^{2+}$ to non-specifically block all $Ca^{2+}$ influx and then exposed to thapsigargin to release ER $Ca^{2+}$ and stimulate $Ca^{2+}$ influx. Cytoplasmic $Ca^{2+}$ levels were followed over time. Tg releases ER $Ca^{2+}$ in all cases but subsequent store-operated $Ca^{2+}$ influx is blocked in cells pre-incubated with $Ni^{2+}$. A: HL60 cells infected with vector control or ABC50 shRNA treated with Tg. B: HL60 cells infected with vector control or ABC50 shRNA pre-incubated in $Ni^{2+}$ to block influx, and then treated with Tg. C: HL60 cells infected with vector control or ABC50 overexpressing virus treated with Tg. D: HL60 cells infected with vector control or ABC50 overexpressing virus pre-incubated in $Ni^{2+}$ to block influx, and then treated with Tg.

It was previously demonstrated that the Ec resistance phenotype of E2R2 cells was associated with altered $Ca^{2+}$ physiology. Specifically, E2R2 cells displayed unchanged ER $Ca^{2+}$ store content, but increased $Ca^{2+}$ influx in response to ER $Ca^{2+}$ store depletion by the ATPase ER $Ca^{2+}$ pump inhibitor thapsigargin[10]. To investigate the effect of altered ABC50 expression on $Ca^{2+}$ physiology, ER $Ca^{2+}$ content and influx was measured in ABC50 knockdown and overexpressing cells. As shown in FIG. 5, no differences in either ER $Ca^{2+}$ content (FIG. 5B, D) or Tg-stimulated $Ca^{2+}$ influx (FIG. 5A, C) were observed in ABC50 KD or overexpressing cells. These observations indicate that ABC50 does not directly affect $Ca^{2+}$ physiology in HL60 cells.

ER Stress Response in ABC50 Knockdown or Overexpressing Cells.

Ec, Tg and Tu are all potent inducers of ER stress. To compare the ER stress response of cells with altered ABC50 expression, cells were treated for 60 minutes with the ER stress agents and levels of phosphorylated eIF2α and the chaperone BiP, two classic indicators of ER stress, were determined by Western blot. As shown in FIG. 6A, increased levels of phosphorylated eIF2α were observed in treated ABC50 knockdown cells compared to vector control. Ec and Tg were particularly effective at inducing increased levels of eIF2α. Induction of BiP expression by ER stress agents was not affected by ABC50 knockdown (FIG. 6B) although basal levels were slightly increased compared to control. In contrast, ABC50 overexpressing cells displayed reduced levels of phosphorylated eIF2α when exposed to Ec, Tg and Tu (FIG. 6C). BiP expression was little changed in response to the ER stress agents compared to control (FIG. 6D) with no observed difference in background expression. Taken together, the divergence of response between eIF2α phosphorylation and BiP induction suggests that the effect of ABC50 is specific for the eIF2α response.

Ribosomal Content and Protein Synthesis in ABC50 Knockdown or Overexpressing Cells.

Figure 7:
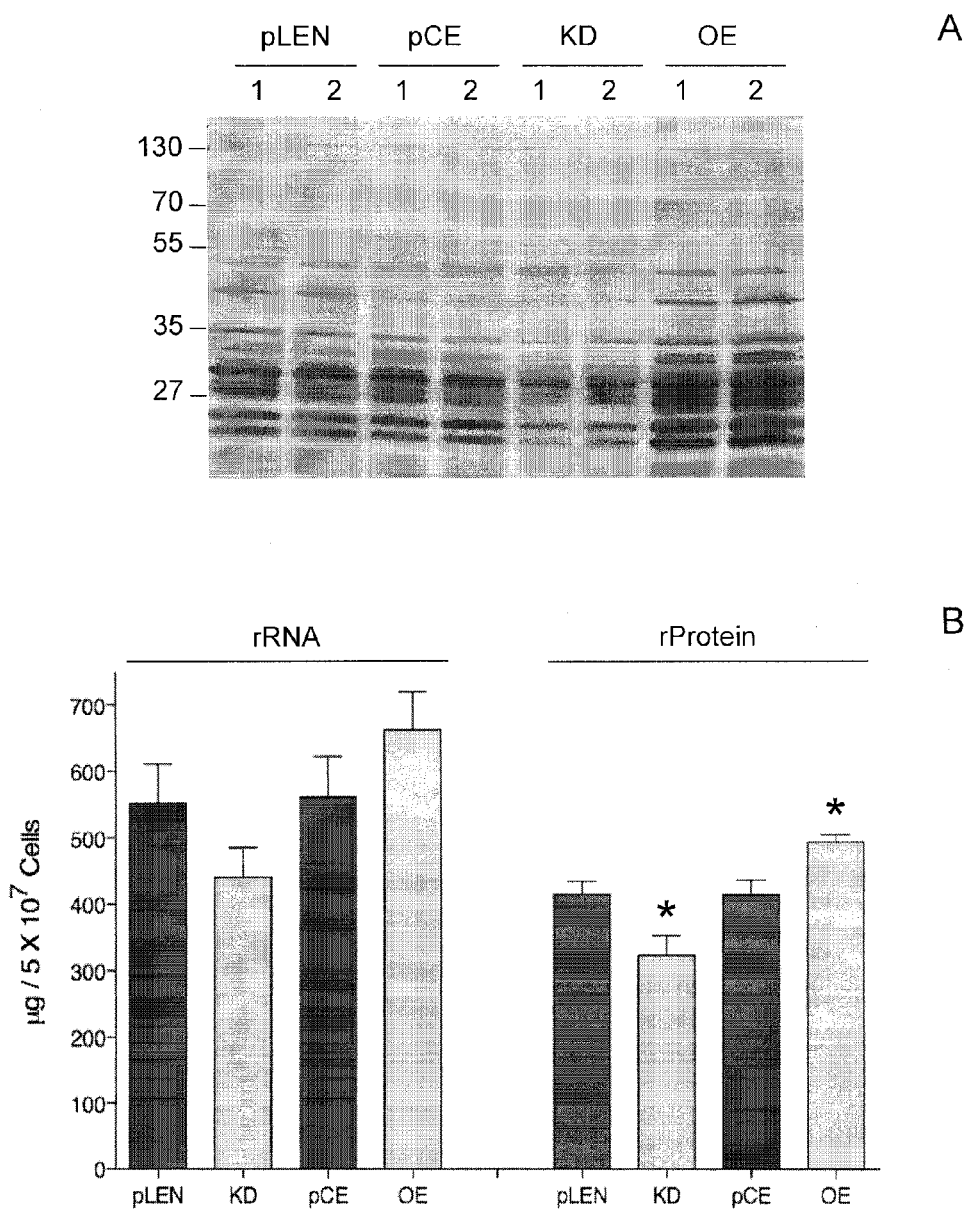
FIG. 7 Effect of ABC50 knockdown or overexpression on ribosomal RNA and Protein content. Ribosomes were purified as described in the Materials and Methods. A: Total ribosomal proteins obtained from 2 independent cultures and extractions were analyzed by electrophoresis on a 12% SDS-PAGE gel. The gel was then stained with Coomassie Brilliant Blue to visualize the protein bands. B: rRNA and rProtein content as measured by absorbance.
Figure 8:
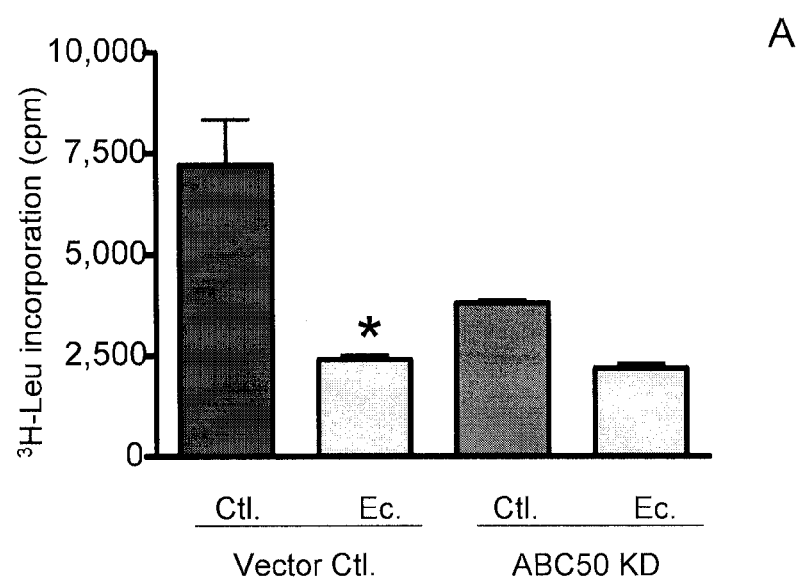
FIG. 8 Effect of ABC50 knockdown or overexpression on global protein synthesis. Cells were incubated with 15 µM Ec for 15 minutes, pulse-labelled with 3H-leucine and incorporation was measured as described in Materials and Methods. A: Vector control vs ABC50 knock-down. B: Vector control vs ABC50 overexpression. The values are averages and standard errors from 4 replicates. This experiment was repeated six times. $*p<0.05$, $**p<0.01$ comparing knockdown or overexpressing cells to their vector control.
Figure 8:
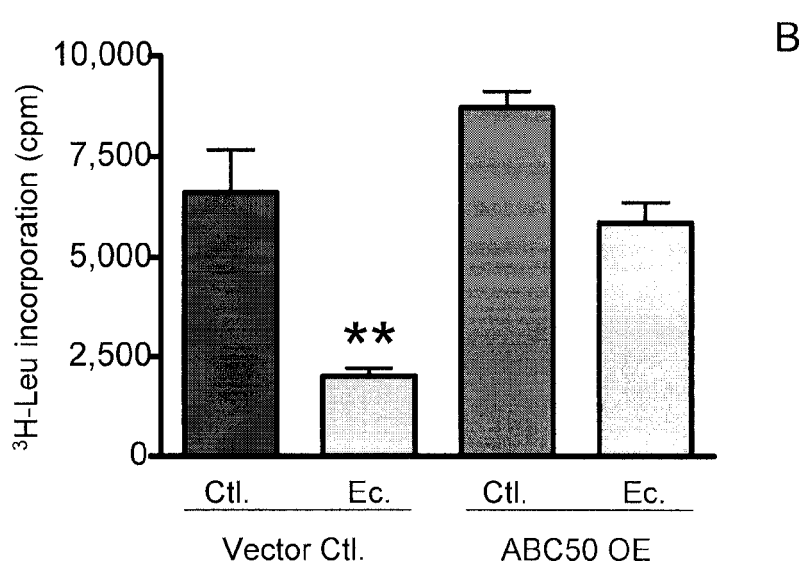

Two major biochemical differences observed previously in Ec-resistant cells were increased ribosomal content and sustained protein synthesis in response to Ec [10]. As shown in FIGS. 7A and B, a trend was observed toward decreased ribosomal RNA and Protein in ABC50 knockdown cells and increased levels in ABC50 overexpressing cells. To test the effect of altered ABC50 expression on protein synthesis, ABC50 knock-down or overexpressing cells were exposed to Ec and global protein synthesis rates were measured. As shown in FIG. 8A, exposure of control cells to Ec resulted in a significant decrease in protein synthesis levels. Interestingly, ABC50 knock down cells displayed a lower base rate of protein synthesis compared to control. Addition of Ec reduced protein synthesis rates even further. In contrast, ABC50 overexpressing cells displayed a slightly higher level of protein synthesis compared to control cells and this level was significantly less reduced after exposure to Ec (FIG. 8B). Taken together, these observations indicate that altered ABC50 expression affects ribosomal content, basal protein synthesis and modifies the cellular response to Ec on protein synthesis.

Enhanced IgG Production in ABC50 Overexpressing Hybridoma Cells.

Figure 9:
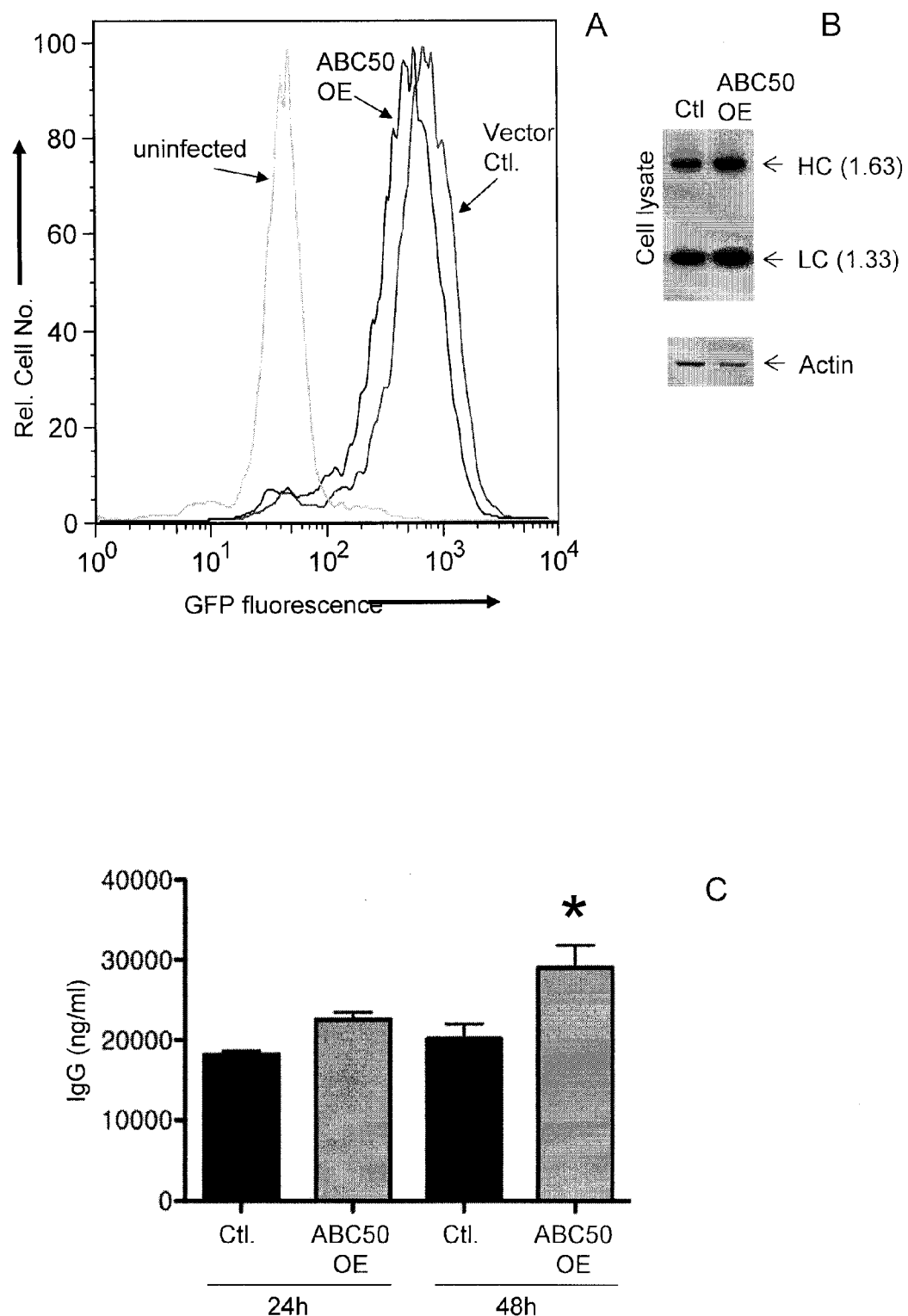
FIG. 9 ABC50 overexpression increases IgG production in hybridoma GK1.5. A: GK1.5 cells were infected with empty vector control or ABC50 overexpressing virus, then sorted for GFP expression. GFP expression levels were measured by flow cytometry. B: Control or ABC50 overexpressing cells were seeded at $1 \times 10^6$ cells/ml, cultured for 24 hours, the cells were pelleted, lysed in RIPA buffer with protease inhibitors and cell lysates were resolved by SDS-PAGE and blotted with rabbit anti-sera specific for heavy and light chains. H: antibody heavy chain, L: antibody light chain. The numbers in brackets represent the ratio of band intensities (as determined by densitometry) for ABC50 overexpressing vs control. The ratio is the average of three independent measurements. C: Cell supernatants were collected at 24 and 48 hours and IgG levels were measured by ELISA. The values are averages of two determinations. This experiment was repeated three times. $*p<0.05$ comparing overexpressing cells to their vector control.

The observation that ABC50 expression influenced global protein synthesis levels suggested that it might also affect expression of individual proteins. This property might be of utility in enhancing production of useful proteins, particularly in cells expressing high amounts of specific proteins such as hybridomas. To test this possibility, hybridoma cell line GK1.5 was infected with the ABC50-expressing lentivirus, infected cells were sorted using GFP expression as a marker of infection (FIG. 9A) and antibody production was measured by Western blotting and ELISA. As shown in FIG. 9B, GK1.5 cells infected with the ABC50 expressing virus produced significantly more antibody heavy and light chains compared to vector control. ELISA analysis of antibody concentrations secreted into the supernatant indicated that antibody production was 44% higher at 48 h in ABC50 overexpressing cells compared to control cultures. (FIG. 9C). This result suggests that ABC50 is useful in boosting protein expression of specific gene products like antibody heavy and light chains.

Selection for Ec Resistance in sp2 Cells Results in Multidrug Resistance and Increased ABC50 Expression.

Figure 10:
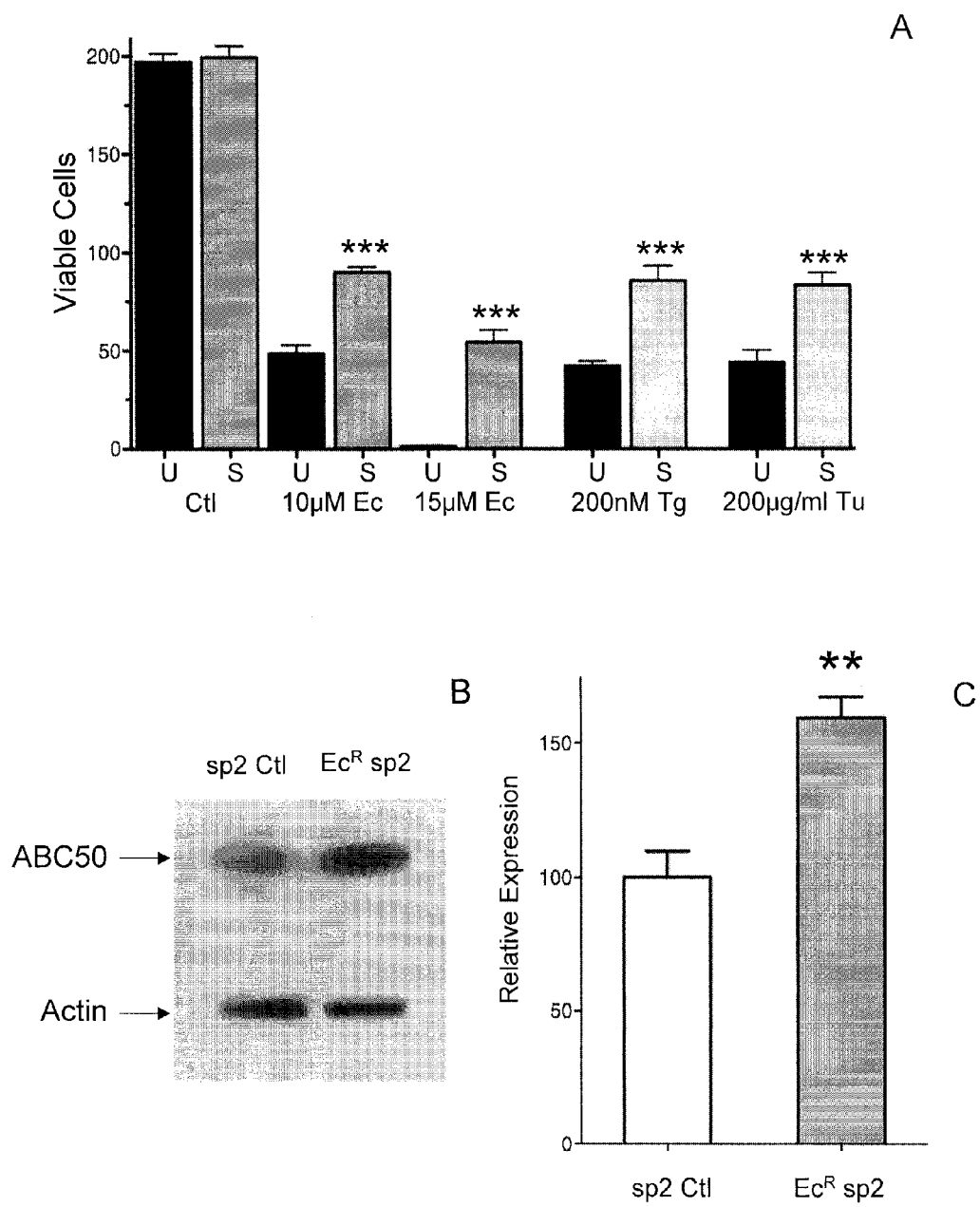
FIG. 10. Generation of Ec-resistant sp2 cells. Sp2 cells were exposed to increasing concentrations of Econazole. Cells remaining after treatment were expanded and subjected to additional rounds of selection. A: cell viability for unselected (U) and selected (S) cells. Exposure to Econazole was for 2 hours in low serum medium, followed by a recovery period of 24 hours in full growth medium. Cells were exposed to Thapsigargin (Tg) and Tunicamycin (Tu) overnight. Cell viability was determined by Trypan Blue staining of 200 cells. B: Western blot of ABC50 expression in sp2 cells selected for resistance to Ec showing increased expression. C: Quantitation of expression normalized to actin. $p<0.01$, $*p<0.001$ comparing selected vs unselected.

Sp2 cells are commonly used as fusion partners for creating hybridomas. The ability to generate sp2 cells that are generally resistant to ER stress and overexpress ABC50 would therefore be of use in the process of hybridoma generation. To this end, sp2 cells were exposed to increasing concentrations of Ec as described above for HL60 cells. Their sensitivity to ER stress agents was then characterized. As shown in FIG. 10a, Ec-resistant sp2 cells were also found to be relatively resistant to the other ER stress agents Tg and Tu. Furthermore, expression analysis (FIGS. 10B,C) indicates that ABC50 is also overexpressed in these cells. These observations therefore indicate that Ec selection is useful for selecting ER stress resistant and ABC50 overexpressing cells.

Discussion

Ec induces ER stress and cell death through the sustained depletion of ER $Ca^{2+}$ stores. This is caused by blocking $Ca^{2+}$ influx at the plasma membrane and stimulating ER $Ca^{2+}$ release through ROS generation at the mitochondria. One consequence of this $Ca^{2+}$ depletion effect is profound inhibition of protein synthesis. The generation and characterization of Ec-resistant mutants further supported the importance of $Ca^{2+}$ depletion and protein synthesis inhibition by demonstrating increased influx and increased ribosomal content and function in resistant cells. A role for the protein ABC50 in Ec resistance is disclosed. ABC50 is herein identified as an overexpressed gene in Ec-resistant E2R2 cells. Western blot analysis demonstrated that protein levels were increased by 65% compared to WT cells. Sp2 cells similarly selected for Ec resistance were also observed to be multi-drug resistant and to overexpress ABC50. Knockdown of ABC50 in both HL60 and E2R2 cells increased sensitivity to Ec indicating that ABC50 contributes to resistance. ABC50 was also found to modulate sensitivity to Tg and Tu, other ER stress agents but not serum withdrawal or etoposide. ABC50 knockdown had no effect on ER $Ca^{2+}$ content and influx, but reduced ribosomal content and protein synthesis in knock-down cells and increased ribosomal content and protein synthesis in HL60 cells overexpressing the protein. Taken together, these results indicate that ABC50 affects sensitivity to Ec and other ER stress agents, likely through its effects on protein synthesis.

It is of interest to contrast the effect of ABC50 knock-down with ABC50 overexpression. While the knock-down significantly increased ER stress indicators eIF2α and BiP, decreased protein synthesis and increased sensitivity to Ec, overexpression only slightly relieved ER stress indicators and increased protein synthesis and had only a modest effect on Ec sensitivity. The observation of effects on protein synthesis through ABC50 overexpression differs from the recent work of Paytubi et al. who observed a lack of effect on protein synthesis after overexpressing ABC50 in HEK293 cells[3]. Without wishing to be bound by theory, these observations indicate that a reduction in its protein level may make ABC50 rate-limiting for protein synthesis while the modest effect from overexpression indicates that ABC50 is not normally rate-limiting. As well, while ABC50 overexpression did partially prevent full inhibition of protein synthesis by Ec, this effect was insufficient to provide significant protection from Ec-induced apoptosis. This observation may indicate that full resistance to Ec requires both altered $Ca^{2+}$ influx as well as increased protein synthesis.

Manipulating ABC50 expression levels was shown to also alter sensitivity to the classic ER stress inducers Tg and Tu. Tg, like Ec, depletes the ER of $Ca^{2+}$. However unlike Ec, which blocks $Ca^{2+}$ influx, ER depletion by Tg overstimulates influx resulting in very high cytoplasmic $Ca^{2+}$ levels (FIGS. 5A,C). This $Ca^{2+}$ overload response likely contributes significantly to Tg-induced apoptosis, as documented previously in mast cells[4]. Therefore the partial effect of ABC50 knockdown on Tg sensitivity may reflect the relative importance of $Ca^{2+}$ overload compared to ER stress in Tg toxicity. Tu is a glycosylation inhibitor and induces ER stress through the Unfolded Protein Stress Response[12,13]. Since one consequence of ER stress induction is suppression of protein synthesis, it is possible that ABC50 knockdown promotes Tu toxicity through a combined effect on protein synthesis. Nevertheless, the fact that ABC50 overexpression partially protects cells from Ec, Tg and Tu indicates that its overexpression contributed to the multi-drug resistance phenotype of E2R2 cells.

Figure 6:
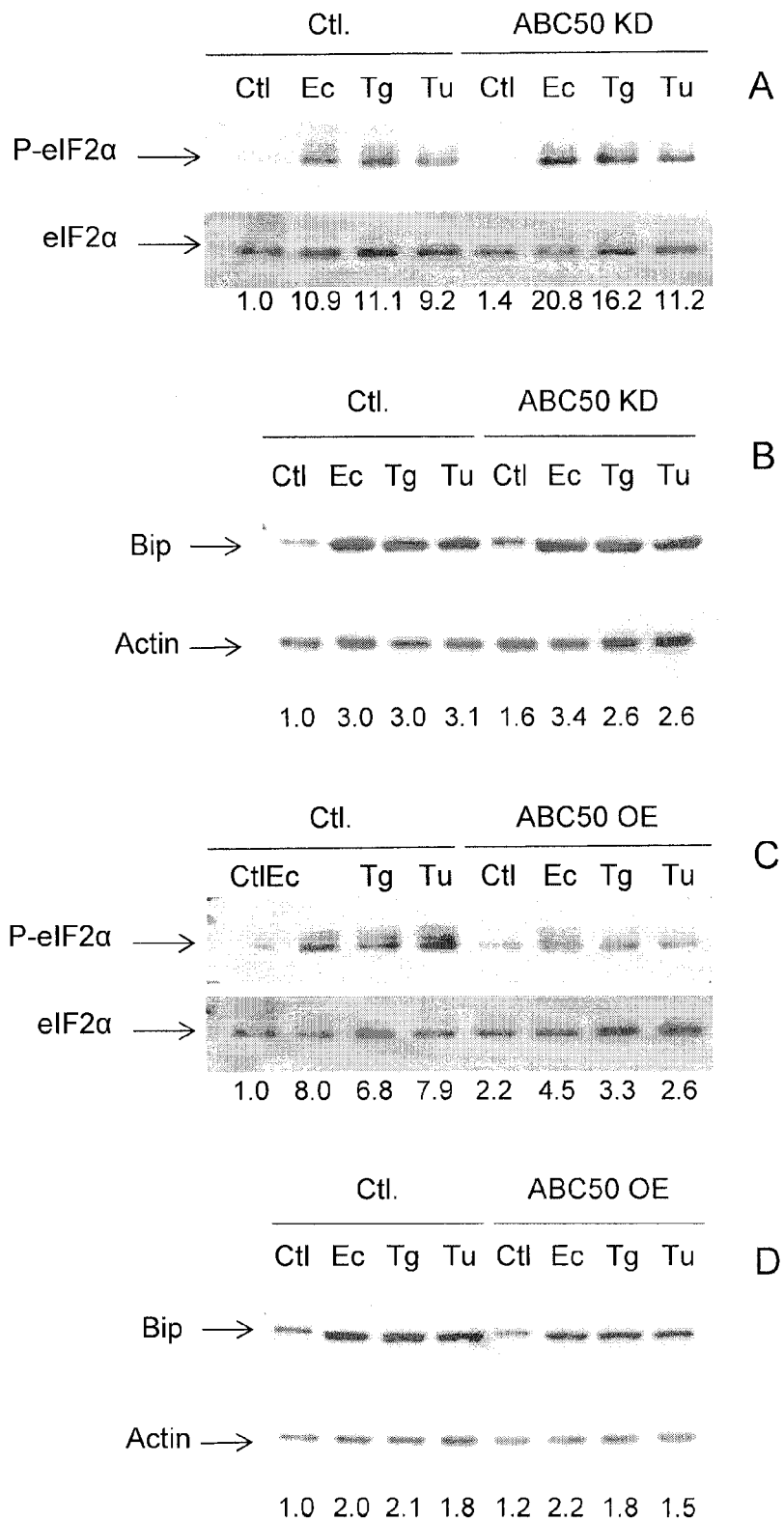
FIG. 6. ABC50 knockdown or overexpression alters the ER stress response. Vector controls, knockdown (A, B) or overexpressing cells (C, D) were exposed to Ec (15 µM), Tg (200 nM) or Tu (200 ng/ml) for 60 minutes. The cells were collected, lysed in RIPA buffer, resolved by SDS-PAGE and analysed with anti-sera specific for A, C: ser51-phosphorylated eIF2α or total eIF2α, B, D: BiP or actin. Numbers represent relative expression levels compared to control normalized to either total eIF2α or actin. The blots are representative of two independent experiments.

As shown in FIG. 6, increased phosphorylation of eIF2α was observed in response to ER stress when ABC50 was knocked down, and decreased levels when ABC50 was overexpressed. Tyzack et al.[2] previously commented that they did not observe any effect of ABC50 on eIF2α phosphorylation by RNA PK in vitro. Without wishing to be bound to theory, the observation that eIF2 phosphorylation is modulated by ABC50 may reflect the unique environment of ER stressed cells. Alternatively, the effects of ABC50 on eIF2α phosphorylation may be an indirect effect associated with altered cellular stress due to insufficient (or excess) ABC50. The fact that BiP induction is little changed when ABC50 expression is altered argues against a general effect on ER stress.

Ribosomal biogenesis is tightly regulated during growth through the mTOR pathway[14,15]. Cellular stress can also influence ribosome biogenesis through both mTOR and JNK-mediated phosphorylation of the TIF-IA transcription factor[16], resulting in inhibition of rDNA transcription. The observation of reduced and increased ribosomal content in ABC50 KD or overexpressing cells respectively is unlikely to reflect growth conditions, since growth rate in both cases appeared to be similar to WT. It is possible that altered ribosomal content reflects differences in basal stress levels, as indicated by increased BiP and phospho-eIF2α levels in ABC50 KD cells.

Although modest, the increased level of protein synthesis due to ABC50 overexpression translated into a significant increase in antibody production by the hybridoma GK1.5. Therefore, increasing ABC50 expression is useful for boosting expression of specific proteins of interest such as antibody heavy and light chains. Interestingly, Ota et al.[17] recently identified a genetic linkage between the ABC50 gene locus and increased susceptibility to autoimmune pancreatitis. Since the phenotype of these patients includes increased serum titers of $IgG_4$, it is possible that ABC50 polymorphisms may contribute to this disease by enhancing antibody production.

ABC50 contributes significantly to Ec resistance. Its mechanism of action appears to be primarily through its modulation of protein synthesis.

Materials and Methods

Cells and Cell Culture

Human HL60 promyelocytic leukemia cells, their E2R2 derivative and GK1.5 hybridoma cells [18] were cultured in RPMI 1640 medium supplemented with 10% FBS and antibiotics.

Growth Curves

Cells were grown in duplicate cultures at the initial concentration of $0.4 \times 10^6$ in RPMI containing 10% FCS. Cells were collected and counted at the 24, 48 and 72 hour time intervals.

Apoptosis

To measure apoptosis induced by Econazole (Ec; Sigma-Aldrich, St. Louis, Mo.), cells were treated with Ec in RPMI containing 1% FBS for 2 hours at 37° C. then further incubated overnight in RPMI containing 10% FBS. Apoptosis induced by thapsigargin (Tg; Sigma-Aldrich) or Tunicamycin (Tu; Sigma-Aldrich) was determined after overnight incubation in RPMI containing 1% FBS. The cells were washed with PBS and stained with Annexin V-cy5 Apoptosis Detection kit (Biovision. Inc., Mountain View, Calif.)/PI and analysed by flow cytometry.

Differential Display

Differential Display [11] comparing mRNA from HL60 vs Ec-resistant E2R2 cells was performed using the Delta Differential Display Kit from Clontech. All procedures were performed according to the manufacturer's instructions and involved using pairwise combinations of 10 Arbitrary primers with 9 Oligo dT primers. Differentially expressed bands were excised from the gel, re-amplified, TA-cloned and sequenced.

Reverse Northern Analysis

3 µg of plasmid DNA from each sample was boiled, rapidly placed on ice, then dotted through a dot blot manifold onto duplicate pre-soaked nylon membranes. The membranes were U.V. cross-linked, incubated in pre-hybridization solution (5×SSC, 5×Denhardt's solution, 50 mM PBS (pH 7.0), 0.2% SDS, 500 µg/ml salmon sperm DNA, 50% formamide). The membranes were hybridized in hybridization solution (5×SSC, 5×Denhardt's solution, 50% formamide) containing $6.5 \times 10^7$ cpm of $^{32}PdCTP$-labelled reverse-transcribed cDNA probe from either HL60 or E2R2 total RNA. The blots were hybridized overnight, washed in 2×SSC and then 2×SSC, 0.1% SDS until background radiation was reduced. The blots were exposed to x-ray film for visualization.

Construction of Lentivirus Vectors

The empty lentivirus vector pLEN (H1GFP), in which the H1 promoter drives expression of shRNA sequences was a gift from Dr. John Dick (University Health Network, Toronto, Canada). The sequences of the oligos used to knock down ABC50 expression were: 5'TAAGCTGTCATCTGGCTTAATAAGGATCCTTATTAAGCCAGATGA CAGCTTTTT3' (SEQ ID NO:3) and 5'CTAGAAAAAGCT-GTCATCTGGCTTAATAAGGATCCTTAT-TAAGCCAGATGA CAGCTTAAT3' (SEQ ID NO:4). Each pair of oligos were mixed and annealed by incubating at 95° C. for 5 min and cooling slowly. The annealed mixture was ligated into pLEN vector that had been digested with PacI and XbaI.

Construction of Lentivirus Over-Expressing ABC50

The ABC50 clone 7 (obtained from Dr. A. Beaulieu, University of Laval, Quebec, Canada, missing 4 nt from the 5' end) (GenBank Accession number: AF027302; gi: 2522533) was used as the template for cloning the ABC50 structural gene by PCR amplification. To add the 4 nt at the 5', two primers were used: Forward: 5'-AT CCCGGG ATGC CGA AGG CGC CCA AGC AGC AGC -3' (SEQ ID NO:9)(contains XmaI site); Reverse: 5'-AT CTCGAG TCAC TCT CGG GGC CGG CTG ACC -3' (SEQ ID NO:10) (contains XhoI site). The amplified ABC50 structural gene was first cloned into pCR4Blunt-TOPO vector (Invitrogen) then subcloned into the pCE lentivirus expression vector (Dr. John Dick, UHN, Toronto) that has been digested with XmaI and XhoI. The whole ABC50 gene was sequenced to confirm the lack of mutations.

Generation of the Infective Lentivirus

Lentivirus vectors harboring human ABC50 shRNA or the ABC50 structural gene were produced by transient transfection into 293T cells as previously described [19]. Briefly, the backbone plasmid vector construct (10 µg) was mixed with the accessory plasmids VSVG (3.5 µg), pRRE (6.5 µg) and pREV (2.5 µg) and transfected into 293T cells with the Calphos Mammalian Transfection Kit (Clontech, Mountain View, Calif.). The cell supernatant was replaced with 4 ml fresh Iscove MEM (10% FCS) at 24 hours and virus was harvested at 48 hours after the plasmid transfection.

Lentiviral Infection

A total of $0.1 \times 10^6$ HL60 cells were infected with 2 ml lentivirus culture supernatant ($\sim 2 \times 10^6$ virus particles) in the presence of 8 µg/ml polybrene (Sigma-Aldrich, St. Louis, Mo.) for 4 days. Up to 94% of cells were positive for GFP expression. GFP positive cells were sorted by fluorescence activated cell sorting and grown in RPMI (10% FBS) for further analysis.

Western Blot

Cells were washed with PBS and lysed with Triple lysis buffer (50 mM Tris pH7.0, 150 mM NaCl, 0.1% SDS, 1% NP-40 and 0.5% DOC). Proteinase inhibitor (Boehringer) was added to 10 ml lysis buffer before use. Protein concentration was determined with the Pierce BCA kit. 20 µg of total protein was loaded onto 10% SDS-PAGE, transferred onto filters and blotted with rabbit anti-human ABC50 polyclonal serum (kind gift from Dr. C. Proud, Vancouver, Canada). eIF2α and its phosphorylated form (Ser51) were detected with rabbit polyclonal antibodies from Cell Signalling (Danvers, Mass.). Mouse anti-BiP/GRP78 antibodies were obtained from BD Biosciences (San Jose, Calif.) Anti-actin (pan Ab-5, Clone ACTN05) (Labvision/Neomarker, Fremont, Calif.) was used as a loading control.

$Ca^{2+}$ Measurement $[Ca^{2+}]_c$ measurements were performed by flow cytometry. Cells ($5 \times 10^5$ cells/ml) were serum-deprived for ~2 hours in Tyrode's buffer [HEPES (10 mM), NaCl (100 mM), KCl (5 mM), $CaCl_2$ (1.4 mM), $MgCl_2$ (1 mM), glucose (5.6 mM), BSA (0.05%)]. Cells were then incubated in Indo-1 loading buffer (30 min, 37° C.; 5 µM Indo-1AM, 0.03% pluronic F-127 in Tyrode's buffer), washed (2 times) and incubated at room temperature (greater than 15 min) to allow for the complete removal and/or conversion of Indo-1AM to $Ca^{2+}$-sensitive Indo-1. Measurements were performed using a laser tuned to 338 nm while monitoring emissions at 405 nm and 450 nm. The concentration of intracellular free $Ca^{2+}$ was calculated according to the following formula [20]:

$$[Ca^{2+}]_i = K_d \times (F_{min}/F_{max}) \times (R - R_{min})/(R_{max} - R),$$

where R is the ratio of the fluorescence intensities measured at 405 nm and 450 nm during the experiments and F is the fluorescence intensity measured at 450 nm. $R_{min}$, $R_{max}$, $F_{min}$ and $F_{max}$ were determined from in situ calibration of unlysed cells using 4 μM ionomycin in the absence ($R_{min}$ and $F_{min}$; 10 mM EGTA) and presence of ($R_{max}$ and $F_{max}$) of $Ca^{2+}$. $K_d$ (250 nM) is the dissociation constant for Indo-1 at 37° C. $R_{min}$, $R_{max}$, $F_{min}$ and $F_{max}$ varied depending upon settings and were determined at the beginning of each experimental procedure.

Protein Synthesis

Cells ($2\times10^5$/sample) were collected, washed with PBS and then re-suspended in RPMI supplemented with fatty acid-free bovine serum albumin (BSA; 0.05%; Sigma). Cells were treated with Ec (0, 15 μM) for 15 min. After centrifugation (2,500 rpm; 5 min), cells were pulse-labeled with [$^3$H]-leucine (50 μCi/ml) for 10 min (37° C.; 5% $CO_2$) in leucine-free RPMI. After two washes in RPMI, pellets were lysed with Triton X-100 (0.5% in PBS) followed by trichloroacetic acid (TCA, 10% w/v; 4° C.). Samples were washed in TCA (5% w/v), and the protein pellets were re-suspended in microscintillant (Packard, Conn., USA) and measured using a microplate scintillation counter (Packard).

Ribosomal Purification $5\times10^7$ HL-60 cells growing in log phase were collected, washed with cold PBS, and fractionated according to the method described by Greco and Madjar [21]. The ribosomal fraction was isolated through centrifugation of post mitochondrial supernatants on top of a 1 M sucrose cushion at 245,000×g to pellet the ribosomes. The ribosome pellets were resuspended in 300 μl of RIPA buffer and disrupted by incubation in 60 mM EDTA on ice for 30 min. The concentration of the total ribosomal protein was calculated based on the absorbance of the samples (A280). Ribosomal RNAs were extracted with TRIzol and the concentration was measured by a spectrophotometer at A260.

IgG Measurements

IgG levels produced by the rat hybridoma GK1.5 (ATCC no. TIB-207) were measured by Western blotting and ELISA. For Western blotting, cells were plated at a concentration of $1\times10^6$ cells/ml in growth medium for 24 hours. The cells were then collected, counted, pelleted and cell lysates were prepared in RIPA buffer with protease inhibitors (Sigma). Lysates and cell supernatants were resolved on 10% SDS-PAGE and transferred to PVDF membranes. Antibody heavy and light chains were detected with HRP-conjugated rabbit anti-rat IgG (H+L) (Zymed; San Francisco, Calif.). For ELISA measurements, Goat anti-rat IgG or normal control IgG from Goat serum (Sigma) were diluted to 5 μg/ml in coating buffer (50 mM Tris, 150 mM NaCl, pH9.5), placed into a 96 well ELISA plate in 50 μl volume and incubated for 40 min at room temperature. The plate was washed for 8 times with distilled water and incubated with 50 μl of PBS containing 3% FBS for additional 40 min at room temperature. Empty vector and ABC50 over-expressed lentivirus transfected GK1.5 hybridoma cells were grown in Iscove's Modified Dulbecco's Medium (IMDM) containing 10% FBS. Cell culture supernatant was collected and diluted in same media and 50 μl diluted samples were added into the 96-well plate. Normal rat IgG from rat serum (Sigma) was used for determining the standard curve. After incubating for 2 hours at room temperature, the wells were washed 8 times with distilled water. HRP conjugated Goat anti-rat IgG (Sigma) was diluted 1:2000 in IMDM and 50 μl reagent was added, incubated for another 40 min. and washed as described above. 100 μl of substrate 3,3_,5,5_-Tetramethylbenzidine (TMB) (Sigma) was added and the reaction was stopped with 0.5 M $H_2SO_4$ when a yellow color developed (5 to 10 min). The plate was read at 450 nM with an ELISA reader.

Statistical Analysis

Where indicated, statistical significance was determined using the Student's t-test. $p<0.05$ (*), $p<0.01$ () and $p<0.001$(*) were as indicated.

Example 2

Methods of Producing a Protein of Interest

There are various methods to effect expression of a protein of interest. For example, a cell expressing a protein of interest, endogenous or heterologous can be transfected/transduced with an expression vector or infected with a virus to introduce a ABC50 polynucleotide encoding a ABC50 protein or fragment having protein synthesis increasing activity. For example, a method can comprise:

Transfect/transduce cells expressing a protein of interest with the ABC50 expression vector. Cells could be selected using a drug-resistance marker, or by expression of a co-transduced marker like GFP.

Alternatively, cells overexpressing ABC50 can be made to express the protein of interest. For example, a method can comprise the following:

Overexpress ABC50 in cells, then transfect them with the recombinant protein of interest.

In a further alternative, the protein of interest and ABC50 protein or fragment, can be coexpressed for example by transfect/transduce cells with ABC50 and the protein of interest together.

Further Ec selection can be used to increase ABC50 levels in a cell expressing a protein of interest and/or in a cell into which a polynucleotide encoding a protein of interest is introduced. For example such a method could comprise: select cells that are resistant to Ec and then use them as recipients for further transfection with a protein of interest.

Table: Sequences

1. Examples of Human ABC50 Molecules

A human ABC50 amino acid sequence is provided in SEQ ID NO:1

A human ABC50 nucleotide sequence is provided in SEQ ID NO: 6

2. Examples of Rat ABC50 Molecules

A rat ABC50 amino acid sequence is provided in SEQ ID NO:2

A rat ABC50 nucleotide sequence is provided in SEQ ID NO:7

3. Examples of Mouse ABC50 Molecules

A mouse ABC50 amino acid sequence is provided in SEQ ID NO: 5

A mouse ABC50 nucleotide sequence is provided in SEQ ID NO: 8

4. Examples of Antisense Agents (SEQ ID NO: 3)
5'TAAGCTGTCATCTGGCTTAATAAGGATCCTTATTAAGCCAGATGACAGCTTTTT3'

(SEQ ID NO: 4)
5'CTAGAAAAAGCTGTCATCTGGCTTAATAAGGATCCTTATTAAGCCAGATGACAGCTTAAT3'

5. Examples of Primers for Cloning ABC50

(SEQ ID NO: 9)
5'-AT CCCGGG ATGC CGA AGG CGC CCA AGC AGC AGC-3'
(contains XmaI site);

-continued

```
                                                   (SEQ ID NO: 10)
5'-AT CTCGAG TCAC TCT CGG GGC CGG CTG ACC-3'
(contains XhoI site)
```

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Full Citations for References Referred to in the Specification

1. Richard M, Drouin R, Beaulieu A D. ABC50, a novel human ATP-binding cassette protein found in tumor necrosis factor-alpha-stimulated synoviocytes. Genomics. 1998; 53:137.
2. Tyzack J K, Wang X, Belsham G J, Proud C G. ABC50 interacts with eukaryotic initiation factor 2 and associates with the ribosome in an ATP-dependent manner. J Biol. Chem. 2000; 275:34131.
3. Paytubi S, Morrice N A, Boudeau J, Proud C G. The N-terminal region of ABC50 interacts with eukaryotic initiation factor eIF2 and is a target for regulatory phosphorylation by CK2. Biochem J. 2008; 409:223.
4. Soboloff J, Berger S A. Sustained ER Ca2+ Depletion Suppresses Protein Synthesis and Induces Activation-enhanced Cell Death in Mast Cells. J Biol Chem. 2002; 277:13812.
5. Zhang Y, Soboloff J, Zhu Z, Berger S A. Inhibition of Ca2+ influx is required for mitochondrial reactive oxygen species-induced endoplasmic reticulum Ca2+ depletion and cell death in leukemia cells. Mol. Pharmacol. 2006; 70:1424.
6. Soboloff J, Zhang Y, Minden M, Berger S. Sensitivity of myeloid leukemia cells to calcium influx blockade. Application to bone marrow purging. Exp Hematol. 2002; 30:1219.
7. Zhang Y, Crump M, Berger S A. Purging of contaminating breast cancer cells from hematopoietic progenitor cell preparations using activation enhanced cell death. Breast Cancer Res Treat. 2002; 72:265.
8. Hacker D L, Nallet S, Wurm F M. Recombinant Protein Production Yields from Mammalian Cells: Past, Present, and Future. BioPharm International. 2008
9. Yu Y, Niapour M, Zhang Y, Berger S A. Mitochondrial regulation by c-Myc and hypoxia-inducible factor-1 alpha controls sensitivity to econazole. Mol Cancer Ther. 2008; 7:483.
10. Zhang Y, Berger S A. Increased calcium influx and ribosomal content correlate with resistance to endoplasmic reticulum stress-induced cell death in mutant leukemia cell lines. J Biol. Chem. 2004; 279:6507.
11. Prashar Y, Weissman S M. Analysis of differential gene expression by display of 3' end restriction fragments of cDNAs. Proc Natl Acad Sci USA. 1996; 93:659.
12. Moenner M, Pluquet O, Bouchecareilh M, Chevet E. Integrated endoplasmic reticulum stress responses in cancer. Cancer Res. 2007; 67:10631.
13. Zhang K, Kaufman R J. From endoplasmic-reticulum stress to the inflammatory response. Nature. 2008; 454: 455.
14. Mayer C, Zhao J, Yuan X, Grummt I. mTOR-dependent activation of the transcription factor TIF-IA links rRNA synthesis to nutrient availability. Genes Dev. 2004; 18:423.
15. Xiao L, Grove A. Coordination of Ribosomal Protein and Ribosomal RNA Gene Expression in Response to TOR Signaling. Curr Genomics. 2009; 10:198.
16. Mayer C, Bierhoff H, Grummt 1. The nucleolus as a stress sensor: JNK2 inactivates the transcription factor TIF-IA and down-regulates rRNA synthesis. Genes Dev. 2005; 19:933.
17. Ota M, Katsuyama Y, Hamano H, Umemura T, Kimura A, Yoshizawa K, Kiyosawa K, Fukushima H, Bahram S, Inoko H, Kawa S. Two critical genes (HLA-DRB1 and ABCF1) in the HLA region are associated with the susceptibility to autoimmune pancreatitis. Immunogenetics. 2007; 59:45.
18. Wilde D B, Marrack P, Kappler J, Dialynas D P, Fitch F W. Evidence implicating L3T4 in class II MHC antigen reactivity; monoclonal antibody GK1.5 (anti-L3T4a) blocks class II MHC antigen-specific proliferation, release of lymphokines, and binding by cloned murine helper T lymphocyte lines. J. Immunol. 1983; 131:2178.
19. Dull T, Zufferey R, Kelly M, Mandel R J, Nguyen M, Trono D, Naldini L. A third-generation lentivirus vector with a conditional packaging system. J. Virol. 1998; 72:8463.
20. Grynkiewcz G, Poenie M, Tsien R Y. A new generation of Ca2+ indicators with greatly improved fluorescence properties. J Biol. Chem. 1985; 260:3440.
21. Greco A, Madjar J J. Cell Biology: A Laboratory Handbook, Vol. 2. J E Celis. 1998
22. Lievremont J P, Rizzuto R, Hendershot L, Meldolesi J. BiP, a major chaperone protein of the endoplasmic reticulum lumen, plays a direct and important role in the storage of the rapidly exchanging pool of Ca2+. J Biol Chem. 1997; 272:30873.

The invention claimed is:

1. A method for increasing the production of an antibody or fragment thereof, said method comprising:
a) introducing into a eukaryotic cell a polynucleotide encoding an ABC50 protein or active fragment thereof having protein synthesis increasing activity and/or eIF2 binding activity and optionally encoding a selectable marker into a eukaryotic cell,
wherein said eukaryotic cell expresses an antibody or a fragment thereof or wherein after the introduction of the polynucleotide encoding an ABC50 protein or active fragment thereof the eukaryotic cell is fused to a second eukaryotic cell expressing an antibody or fragment thereof, thus producing a eukaryotic cell expressing ABC50 protein or active fragment thereof and an antibody or a fragment thereof, and
b) incubating the eukaryotic cell expressing the ABC50 protein or active fragment thereof and the antibody or a fragment thereof under suitable conditions for a suitable length of time to produce the antibody or fragment thereof in the presence of the ABC50 protein such that the antibody or fragment thereof is produced at higher levels than in the absence of the ABC50 protein.

2. A method for increasing the production of an antibody or fragment thereof, said method comprising:
a) chemically inducing the expression of endogenous ABC50 protein in a eukaryotic cell,
wherein said eukaryotic cell expresses an antibody or a fragment thereof or wherein after the chemical induction of the polynucleotide encoding an ABC50 protein the eukaryotic cell is fused to a second eukaryotic cell expressing an antibody or fragment thereof, thus producing a eukaryotic cell expressing ABC50 protein and an antibody or a fragment thereof, and
b) incubating the eukaryotic cell expressing the ABC50 protein and the antibody or a fragment thereof under suitable conditions for a suitable length of time to produce the antibody or fragment thereof in the presence of the ABC50 protein such that the antibody or fragment thereof is produced at higher levels than in the absence of the ABC50 protein.

3. A method for increasing the production of an antibody or fragment thereof, said method comprising:
   a) introducing into a eukaryotic cell a polynucleotide encoding an antibody or fragment thereof and optionally encoding a selectable marker,
   wherein said eukaryotic cell expresses an ABC50 protein or active fragment thereof having protein synthesis increasing activity and/or el F2 binding activity,
   wherein said ABC50 protein or active fragment thereof is recombinantly expressed in the eukaryotic cell after the introduction of the polynucleotide encoding an ABC50 protein or active fragment thereof, thus producing a eukaryotic cell expressing ABC50 protein or active fragment thereof and an antibody or a fragment thereof, and
   b) incubating the eukaryotic cell expressing the ABC50 protein or active fragment thereof and the antibody or a fragment thereof under suitable conditions for a suitable length of time to produce the antibody or fragment thereof in the presence of the ABC50 protein such that the antibody or fragment thereof is produced at higher levels than in the absence of the ABC50 protein.

4. A method for increasing the production of an antibody or fragment thereof, said method comprising:
   a) introducing into a eukaryotic cell a polynucleotide encoding an antibody or fragment thereof and optionally encoding a selectable marker,
   wherein said eukaryotic cell expresses an ABC50 protein,
   wherein said ABC50 protein is expressed by chemically inducing the expression of endogenous ABC50 protein in the eukaryotic cell, thus producing a eukaryotic cell expressing ABC50 protein or active fragment thereof and an antibody or a fragment thereof, and
   b) incubating the eukaryotic cell expressing the ABC50 protein and the antibody or a fragment thereof under suitable conditions for a suitable length of time to produce the antibody or fragment thereof in the presence of the ABC50 protein such that the antibody or fragment thereof is produced at higher levels than in the absence of the ABC50 protein.

5. A method for increasing the production of an antibody or fragment thereof, said method comprising:
   a) introducing into a eukaryotic cell a polynucleotide encoding an ABC50 protein or active fragment thereof having protein synthesis increasing activity and/or eIF2 binding activity and optionally encoding a selectable marker into a eukaryotic cell,
   b) introducing into the eukaryotic cell produced in step a) a polynucleotide encoding an antibody or fragment thereof and optionally encoding a selectable marker,
   thus producing a eukaryotic cell expressing ABC50 protein or active fragment thereof and an antibody or a fragment thereof, and
   c) incubating the eukaryotic cell expressing the ABC50 protein or active fragment thereof and the antibody or a fragment thereof under suitable conditions for a suitable length of time to produce the antibody or fragment thereof in the presence of the ABC50 protein or active fragment thereof such that the antibody or fragment thereof is produced at higher levels than in the absence of the ABC50 protein or active fragment thereof.

6. A method for increasing the production of an antibody or fragment thereof, said method comprising:
   a), chemically inducing the expression of endogenous ABC50 protein in a eukaryotic cell, and
   b) introducing into the eukaryotic cell produced in step a) a polynucleotide encoding an antibody or fragment thereof and optionally encoding a selectable marker,
   thus producing a eukaryotic cell expressing ABC50 protein or active fragment thereof and an antibody or a fragment thereof, and
   c) incubating the eukaryotic cell expressing the ABC50 protein and the antibody or a fragment thereof under suitable conditions for a suitable length of time to produce the antibody or fragment thereof in the presence of the ABC50 protein such that the antibody or fragment thereof is produced at higher levels than in the absence of the ABC50 protein.

7. The method of claim 1, wherein the antibody or antibody fragment is a heterologous protein.

8. The method of claim 1, wherein the antibody is monoclonal, polyclonal, mammalian, murine, chimeric, humanized, primatized, primate, or human, and/or the antibody is a fragment selected from an immunoglobulin light chain, immunoglobulin heavy chain, immunoglobulin light and heavy chains, Fab, F(ab')2, Fc, Fc-Fc fusion proteins, Fv, single chain Fv, single domain Fv, tetravalent single chain Fv, disulfide-linked Fv, domain deleted, minibody, diabody, a fusion protein of one of the above fragments with another polypeptide or Fc-peptide fusion.

9. The method of claim 1, wherein the method further comprises isolating the antibody or antibody fragment, optionally wherein the antibody or antibody fragment is secreted and is secreted into a culture medium, the method further comprising isolating the secreted protein from the culture medium, or wherein the antibody or antibody fragment is intracellular, the method further comprising lysing the cell and isolating the intracellular antibody or antibody fragment, or wherein the antibody or antibody fragment is membrane or surface bound, the method further comprising solubilizing the cell membrane and isolating the membrane protein or surface bound antibody or antibody fragment.

10. The method of claim 1, wherein the ABC50 protein comprises SEQ ID NO: 1, 2 or 5; or a protein with at least 85%, 88%, 90%, 95%, 99% or 99.5% sequence identity with SEQ ID NO:1, 2 or 5.

11. The method of claim 1, wherein the increased expression is about 5% to about 10%, about 11% to about 20%, about 21% to about 30%, about 31% to about 40%, about 41% to about 50%, 51% to about 60%, 61% to about 70%, 71% to about 80%, about 81% to about 90%, about 91% to about 100%, about 150% to about 199%, about 200% to about 299%, about 300% to about 499%, or about 500% to about 1000%.

12. The method of claim 1, wherein the eukaryotic cell is selected from a yeast, plant, worm, insect, avian, fish, reptile and mammalian cell.

13. The method of claim 12, wherein the mammalian cell is a myeloma cell, a spleen cell, a leukemia cell, a hybridoma fusion partner, or a hybridoma cell.

14. The method of claim 13, wherein the hybridoma fusion partner cell, is fused with a cell expressing the antibody or antibody fragment.

15. The method of claim 13, wherein the leukemia cell is HL-60, or the hybridoma cell is GK1.5.

16. The method of claim 12, wherein the mammalian cell is Sp2, NS0, CHO, Per.c6, or L cell.

17. The method of claim 1, wherein the selectable marker is selected from β-galactosidase, chloramphenicol acetyltransferase, firefly luciferase, an antibiotic resistance gene neomycin and hygromycin, dihydrofolate reductase (DHFR) and glutamine synthetase (GS) and optionally wherein selection comprises amplification of the integrated DNA by exposure of the selected cells to methotrexate (MTX) or methionine sulphoximine (MSX).

18. The method of claim 17, wherein the antibiotic resistance gene is selected from neomycin and hygromycin.

19. The method of claim 2, wherein the antibody or antibody fragment is a heterologous protein.

20. The method of claim 2, wherein the antibody is monoclonal, polyclonal, mammalian, murine, chimeric, humanized, primatized, primate, or human, and/or the antibody is a fragment selected from an immunoglobulin light chain, immunoglobulin heavy chain, immunoglobulin light and heavy chains, Fab, F(ab')2, Fc, Fc-Fc fusion proteins, Fv, single chain Fv, single domain Fv, tetravalent single chain Fv, disulfide-linked Fv, domain deleted, minibody, diabody, a fusion protein of one of the above fragments with another polypeptide or Fc-peptide fusion.

21. The method of claim 2, wherein the method further comprises isolating the antibody or antibody fragment, optionally wherein the antibody or antibody fragment is secreted and is secreted into a culture medium, the method further comprising isolating the secreted protein from the culture medium, or wherein the antibody or antibody fragment is intracellular, the method further comprising lysing the cell and isolating the intracellular antibody or antibody fragment, or wherein the antibody or antibody fragment is membrane or surface bound, the method further comprising solubilizing the cell membrane and isolating the membrane protein or surface bound antibody or antibody fragment.

22. The method of claim 2, wherein the ABC50 protein comprises SEQ ID NO: 1, 2 or 5; or a protein with at least 85%, 88%, 90%, 95%, 99% or 99.5% sequence identity with SEQ ID NO:1, 2 or 5.

23. The method of claim 2, wherein the ABC50 protein is chemically increased by induction of econazole resistance and selecting for ABC50 expressing cells.

24. The method of claim 2, wherein the increased expression is about 5% to about 10%, about 11% to about 20%, about 21% to about 30%, about 31% to about 40%, about 41% to about 50%, 51% to about 60%, 61% to about 70%, 71% to about 80%, about 81% to about 90%, about 91% to about 100%, about 150% to about 199%, about 200% to about 299%, about 300% to about 499%, or about 500% to about 1000%.

25. The method of claim 2, wherein the eukaryotic cell is selected from a yeast, plant, worm, insect, avian, fish, reptile and mammalian cell.

26. The method of claim 25, wherein the mammalian cell is a myeloma cell, a spleen cell, a leukemia cell, a hybridoma fusion partner, or a hybridoma cell.

27. The method of claim 26, wherein the hybridoma fusion partner cell, is fused with a cell expressing the antibody or antibody fragment.

28. The method of claim 26, wherein the leukemia cell is HL-60, or the hybridoma cell is GK1.5.

29. The method of claim 25, wherein the mammalian cell is Sp2, NS0, CHO, Per.c6, or L cell.

30. The method of claim 3, wherein the antibody or antibody fragment is a heterologous protein.

31. The method of claim 3, wherein the antibody is monoclonal, polyclonal, mammalian, murine, chimeric, humanized, primatized, primate, or human, and/or the antibody is a fragment selected from an immunoglobulin light chain, immunoglobulin heavy chain, immunoglobulin light and heavy chains, Fab, F(ab')2, Fc, Fc-Fc fusion proteins, Fv, single chain Fv, single domain Fv, tetravalent single chain Fv, disulfide-linked Fv, domain deleted, minibody, diabody, a fusion protein of one of the above fragments with another polypeptide or Fc-peptide fusion.

32. The method of claim 3, wherein the method further comprises isolating the antibody or antibody fragment, optionally wherein the antibody or antibody fragment is secreted and is secreted into a culture medium, the method further comprising isolating the secreted protein from the culture medium, or wherein the antibody or antibody fragment is intracellular, the method further comprising lysing the cell and isolating the intracellular antibody or antibody fragment, or wherein the antibody or antibody fragment is membrane or surface bound, the method further comprising solubilizing the cell membrane and isolating the membrane protein or surface bound antibody or antibody fragment.

33. The method of claim 3, wherein the ABC50 protein comprises SEQ ID NO: 1, 2 or 5; or a protein with at least 85%, 88%, 90%, 95%, 99% or 99.5% sequence identity with SEQ ID NO:1, 2 or 5.

34. The method of claim 3, wherein the increased expression is about 5% to about 10%, about 11% to about 20%, about 21% to about 30%, about 31% to about 40%, about 41% to about 50%, 51% to about 60%, 61% to about 70%, 71% to about 80%, about 81% to about 90%, about 91% to about 100%, about 150% to about 199%, about 200% to about 299%, about 300% to about 499%, or about 500% to about 1000%.

35. The method of claim 3, wherein the eukaryotic cell is selected from a yeast, plant, worm, insect, avian, fish, reptile and mammalian cell.

36. The method of claim 35, wherein the mammalian cell is a myeloma cell, a spleen cell, a leukemia cell, a hybridoma fusion partner, or a hybridoma cell.

37. The method of claim 36, wherein the hybridoma fusion partner cell, is fused with a cell expressing the antibody or antibody fragment.

38. The method of claim 36, wherein the leukemia cell is HL-60, or the hybridoma cell is GK1.5.

39. The method of claim 35, wherein the mammalian cell is Sp2, NS0, CHO, Per.c6, or L cell.

40. The method of claim 3, wherein the selectable marker is selected from β-galactosidase, chloramphenicol acetyltransferase, firefly luciferase, an antibiotic resistance gene neomycin and hygromycin, dihydrofolate reductase (DHFR) and glutamine synthetase (GS) and optionally wherein selection comprises amplification of the integrated DNA by exposure of the selected cells to methotrexate (MTX) or methionine sulphoximine (MSX).

41. The method of claim 40, wherein the antibiotic resistance gene is selected from neomycin and hygromycin.

42. The method of claim 4, wherein the antibody or antibody fragment is a heterologous protein.

43. The method of claim 4, wherein the antibody is monoclonal, polyclonal, mammalian, murine, chimeric, humanized, primatized, primate, or human, and/or the antibody is a fragment selected from an immunoglobulin light chain, immunoglobulin heavy chain, immunoglobulin light and heavy chains, Fab, F(ab')2, Fc, Fc-Fc fusion proteins, Fv, single chain Fv, single domain Fv, tetravalent single chain Fv, disulfide-linked Fv, domain deleted, minibody, diabody, a fusion protein of one of the above fragments with another polypeptide or Fc-peptide fusion.

44. The method of claim 4, wherein the method further comprises isolating the antibody or antibody fragment, optionally wherein the antibody or antibody fragment is secreted and is secreted into a culture medium, the method further comprising isolating the secreted protein from the culture medium, or wherein the antibody or antibody fragment is intracellular, the method further comprising lysing the cell and isolating the intracellular antibody or antibody fragment, or wherein the antibody or antibody fragment is membrane or surface bound, the method further comprising solubilizing the cell membrane and isolating the membrane protein or surface bound antibody or antibody fragment.

45. The method of claim 4, wherein the ABC50 protein comprises SEQ ID NO: 1, 2 or 5; or a protein with at least 85%, 88%, 90%, 95%, 99% or 99.5% sequence identity with SEQ ID NO: 1, 2 or 5.

46. The method of claim 4, wherein the ABC50 protein is chemically increased by induction of econazole resistance and selecting for ABC50 expressing cells.

47. The method of claim 4, wherein the increased expression is about 5% to about 10%, about 11% to about 20%, about 21% to about 30%, about 31% to about 40%, about 41% to about 50%, 51% to about 60%, 61% to about 70%, 71% to about 80%, about 81% to about 90%, about 91% to about 100%, about 150% to about 199%, about 200% to about 299%, about 300% to about 499%, or about 500% to about 1000%.

48. The method of claim 4, wherein the eukaryotic cell is selected from a yeast, plant, worm, insect, avian, fish, reptile and mammalian cell.

49. The method of claim 48, wherein the mammalian cell is a myeloma cell, a spleen cell, a leukemia cell, a hybridoma fusion partner, or a hybridoma cell.

50. The method of claim 49, wherein the hybridoma fusion partner cell, is fused with a cell expressing the antibody or antibody fragment.

51. The method of claim 49, wherein the leukemia cell is HL-60, or the hybridoma cell is GK1.5.

52. The method of claim 48, wherein the mammalian cell is Sp2, NS0, CHO, Per.c6, or L cell.

53. The method of claim 4, wherein the selectable marker is selected from β-galactosidase, chloramphenicol acetyltransferase, firefly luciferase, an antibiotic resistance gene neomycin and hygromycin, dihydrofolate reductase (DHFR) and glutamine synthetase (GS) and optionally wherein selection comprises amplification of the integrated DNA by exposure of the selected cells to methotrexate (MTX) or methionine sulphoximine (MSX).

54. The method of claim 53, wherein the antibiotic resistance gene is selected from neomycin and hygromycin.

55. The method of claim 5, wherein the antibody or antibody fragment is a heterologous protein.

56. The method of claim 5, wherein the antibody is monoclonal, polyclonal, mammalian, murine, chimeric, humanized, primatized, primate, or human, and/or the antibody is a fragment selected from an immunoglobulin light chain, immunoglobulin heavy chain, immunoglobulin light and heavy chains, Fab, F(ab')2, Fc, Fc-Fc fusion proteins, Fv, single chain Fv, single domain Fv, tetravalent single chain Fv, disulfide-linked Fv, domain deleted, minibody, diabody, a fusion protein of one of the above fragments with another polypeptide or Fc-peptide fusion.

57. The method of claim 5, wherein the method further comprises isolating the antibody or antibody fragment, optionally wherein the antibody or antibody fragment is secreted and is secreted into a culture medium, the method further comprising isolating the secreted protein from the culture medium, or wherein the antibody or antibody fragment is intracellular, the method further comprising lysing the cell and isolating the intracellular antibody or antibody fragment, or wherein the antibody or antibody fragment is membrane or surface bound, the method further comprising solubilizing the cell membrane and isolating the membrane protein or surface bound antibody or antibody fragment.

58. The method of claim 5, wherein the ABC50 protein comprises SEQ ID NO: 1, 2 or 5; or a protein with at least 85%, 88%, 90%, 95%, 99% or 99.5% sequence identity with SEQ ID NO: 1, 2 or 5.

59. The method of claim 5, wherein the increased expression is about 5% to about 10%, about 11% to about 20%, about 21% to about 30%, about 31% to about 40%, about 41% to about 50%, 51% to about 60%, 61% to about 70%, 71% to about 80%, about 81% to about 90%, about 91% to about 100%, about 150% to about 199%, about 200% to about 299%, about 300% to about 499%, or about 500% to about 1000%.

60. The method of claim 5, wherein the eukaryotic cell is selected from a yeast, plant, worm, insect, avian, fish, reptile and mammalian cell.

61. The method of claim 60, wherein the mammalian cell is a myeloma cell, a spleen cell, a leukemia cell, a hybridoma fusion partner, or a hybridoma cell.

62. The method of claim 61, wherein the hybridoma fusion partner cell, is fused with a cell expressing the antibody or antibody fragment.

63. The method of claim 61, wherein the leukemia cell is HL-60, or the hybridoma cell is GK1.5.

64. The method of claim 60, wherein the mammalian cell is Sp2, NS0, CHO, Per.c6, or L cell.

65. The method of claim 5, wherein the selectable marker is selected from β-galactosidase, chloramphenicol acetyltransferase, firefly luciferase, an antibiotic resistance gene neomycin and hygromycin, dihydrofolate reductase (DHFR) and glutamine synthetase (GS) and optionally wherein selection comprises amplification of the integrated DNA by exposure of the selected cells to methotrexate (MTX) or methionine sulphoximine (MSX).

66. The method of claim 65, wherein the antibiotic resistance gene is selected from neomycin and hygromycin.

67. The method of claim 6, wherein the antibody or antibody fragment is a heterologous protein.

68. The method of claim 6, wherein the antibody is monoclonal, polyclonal, mammalian, murine, chimeric, humanized, primatized, primate, or human, and/or the antibody is a fragment selected from an immunoglobulin light chain, immunoglobulin heavy chain, immunoglobulin light and heavy chains, Fab, F(ab')2, Fc, Fc-Fc fusion proteins, Fv, single chain Fv, single domain Fv, tetravalent single chain Fv, disulfide-linked Fv, domain deleted, minibody, diabody, a fusion protein of one of the above fragments with another polypeptide or Fc-peptide fusion.

69. The method of claim 6, wherein the method further comprises isolating the antibody or antibody fragment, optionally wherein the antibody or antibody fragment is secreted and is secreted into a culture medium, the method further comprising isolating the secreted protein from the culture medium, or wherein the antibody or antibody fragment is intracellular, the method further comprising lysing the cell and isolating the intracellular antibody or antibody fragment, or wherein the antibody or antibody fragment is membrane or surface bound, the method further comprising solubilizing the cell membrane and isolating the membrane protein or surface bound antibody or antibody fragment.

70. The method of claim 6, wherein the ABC50 protein comprises SEQ ID NO: 1, 2 or 5; or a protein with at least 85%, 88%, 90%, 95%, 99% or 99.5% sequence identity with SEQ ID NO: 1, 2 or 5.

71. The method of claim 6, wherein the ABC50 protein is chemically increased by induction of econazole resistance and selecting for ABC50 expressing cells.

72. The method of claim 6, wherein the increased expression is about 5% to about 10%, about 11% to about 20%, about 21% to about 30%, about 31% to about 40%, about 41% to about 50%, 51% to about 60%, 61% to about 70%, 71% to about 80%, about 81% to about 90%, about 91% to about 100%, about 150% to about 199%, about 200% to about 299%, about 300% to about 499%, or about 500% to about 1000%.

73. The method of claim 6, wherein the eukaryotic cell is selected from a yeast, plant, worm, insect, avian, fish, reptile and mammalian cell.

74. The method of claim 73, wherein the mammalian cell is a myeloma cell, a spleen cell, a leukemia cell, a hybridoma fusion partner, or a hybridoma cell.

75. The method of claim 74, wherein the hybridoma fusion partner cell, is fused with a cell expressing the antibody or antibody fragment.

76. The method of claim 74, wherein the leukemia cell is HL-60, or the hybridoma cell is GK1.5.

77. The method of claim 73, wherein the mammalian cell is Sp2, NS0, CHO, Per.c6, or L cell.

78. The method of claim 6, wherein the selectable marker is selected from β-galactosidase, chloramphenicol acetyltransferase, firefly luciferase, an antibiotic resistance gene neomycin and hygromycin, dihydrofolate reductase (DHFR) and glutamine synthetase (GS) and optionally wherein selection comprises amplification of the integrated DNA by exposure of the selected cells to methotrexate (MTX) or methionine sulphoximine (MSX).

79. The method of claim 78, wherein the antibiotic resistance gene is selected from neomycin and hygromycin.

\* \* \* \* \*

UNITED STATES PATENT AND TRADEMARK OFFICE
CERTIFICATE OF CORRECTION

| | | |
|---|---|---|
| PATENT NO. | : 8,691,529 B2 | Page 1 of 1 |
| APPLICATION NO. | : 13/318985 | |
| DATED | : April 8, 2014 | |
| INVENTOR(S) | : Stuart A. Berger | |

It is certified that error appears in the above-identified patent and that said Letters Patent is hereby corrected as shown below:

In the Claims

Column 53, line 13, claim 3, "...increasing activity and/or e1 F2 binding..." should read as --...increasing activity and/or eIF2 binding...--

Signed and Sealed this
Seventeenth Day of February, 2015

Michelle K. Lee
*Deputy Director of the United States Patent and Trademark Office*

UNITED STATES PATENT AND TRADEMARK OFFICE
CERTIFICATE OF CORRECTION

PATENT NO.       : 8,691,529 B2                                                Page 1 of 1
APPLICATION NO.  : 13/318985
DATED            : April 8, 2014
INVENTOR(S)      : Stuart A. Berger It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 86 days.

Signed and Sealed this

Twenty-ninth Day of September, 2015

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 845
<212> TYPE: PRT
<213> ORGANISM: Homo sapiens

<400> SEQUENCE: 1

Met Pro Lys Ala Pro Lys Gln Gln Pro Pro Glu Pro Glu Trp Ile Gly
1               5                   10                  15
```

-continued

```
Asp Gly Glu Ser Thr Ser Pro Ser Asp Lys Val Val Lys Gly Lys
            20              25              30
Lys Asp Lys Lys Ile Lys Lys Thr Phe Phe Glu Glu Leu Ala Val Glu
        35              40              45
Asp Lys Gln Ala Gly Glu Glu Lys Val Leu Lys Glu Lys Glu Gln
 50              55              60
Gln Gln Gln Gln Gln Gln Gln Gln Lys Lys Lys Arg Asp Thr Arg
 65              70              75              80
Lys Gly Arg Arg Lys Lys Asp Val Asp Asp Gly Glu Glu Lys Glu
            85              90              95
Leu Met Glu Arg Leu Lys Lys Leu Ser Val Pro Thr Ser Asp Glu Glu
            100             105             110
Asp Glu Val Pro Ala Pro Lys Pro Arg Gly Gly Lys Lys Thr Lys Gly
            115             120             125
Gly Asn Val Phe Ala Ala Leu Ile Gln Asp Gln Ser Glu Glu Glu
    130             135             140
Glu Glu Glu Lys His Pro Pro Lys Pro Ala Lys Pro Glu Lys Asn Arg
145             150             155             160
Ile Asn Lys Ala Val Ser Glu Glu Gln Pro Ala Leu Lys Gly Lys
            165             170             175
Lys Gly Lys Glu Glu Lys Ser Lys Gly Lys Ala Lys Pro Gln Asn Lys
            180             185             190
Phe Ala Ala Leu Asp Asn Glu Glu Asp Lys Glu Glu Ile Ile
    195             200             205
Lys Glu Lys Glu Pro Pro Lys Gln Gly Lys Glu Lys Ala Lys Lys Ala
210             215             220
Glu Gln Gly Ser Glu Glu Gly Glu Gly Glu Glu Glu Glu Glu
225             230             235             240
Gly Gly Glu Ser Lys Ala Asp Asp Pro Tyr Ala His Leu Ser Lys Lys
            245             250             255
Glu Lys Lys Lys Leu Lys Lys Gln Met Glu Tyr Glu Arg Gln Val Ala
            260             265             270
Ser Leu Lys Ala Ala Asn Ala Ala Glu Asn Asp Phe Ser Val Ser Gln
    275             280             285
Ala Glu Met Ser Ser Arg Gln Ala Met Leu Glu Asn Ala Ser Asp Ile
290             295             300
Lys Leu Glu Lys Phe Ser Ile Ser Ala His Gly Lys Glu Leu Phe Val
305             310             315             320
Asn Ala Asp Leu Tyr Ile Val Ala Gly Arg Arg Tyr Gly Leu Val Gly
            325             330             335
Pro Asn Gly Lys Gly Lys Thr Thr Leu Leu Lys His Ile Ala Asn Arg
            340             345             350
Ala Leu Ser Ile Pro Pro Asn Ile Asp Val Leu Leu Cys Glu Gln Glu
    355             360             365
Val Val Ala Asp Glu Thr Pro Ala Val Gln Ala Val Leu Arg Ala Asp
    370             375             380
Thr Lys Arg Leu Lys Leu Leu Glu Glu Glu Arg Arg Leu Gln Gly Gln
385             390             395             400
Leu Glu Gln Gly Asp Asp Thr Ala Ala Glu Arg Leu Glu Lys Val Tyr
            405             410             415
Glu Glu Leu Arg Ala Thr Gly Ala Ala Ala Glu Ala Lys Ala Arg
            420             425             430
Arg Ile Leu Ala Gly Leu Gly Phe Asp Pro Glu Met Gln Asn Arg Pro
            435             440             445
```

Thr Gln Lys Phe Ser Gly Gly Trp Arg Met Arg Val Ser Leu Ala Arg
450                 455                 460

Ala Leu Phe Met Glu Pro Thr Leu Leu Met Leu Asp Glu Pro Thr Asn
465                 470                 475                 480

His Leu Asp Leu Asn Ala Val Ile Trp Leu Asn Asn Tyr Leu Gln Gly
                485                 490                 495

Trp Arg Lys Thr Leu Leu Ile Val Ser His Asp Gln Gly Phe Leu Asp
            500                 505                 510

Asp Val Cys Thr Asp Ile Ile His Leu Asp Ala Gln Arg Leu His Tyr
        515                 520                 525

Tyr Arg Gly Asn Tyr Met Thr Phe Lys Lys Met Tyr Gln Gln Lys Gln
    530                 535                 540

Lys Glu Leu Leu Lys Gln Tyr Glu Lys Gln Lys Lys Leu Lys Glu
545                 550                 555                 560

Leu Lys Ala Gly Gly Lys Ser Thr Lys Gln Ala Glu Lys Gln Thr Lys
                565                 570                 575

Glu Ala Leu Thr Arg Lys Gln Gln Lys Cys Arg Arg Lys Asn Gln Asp
                580                 585                 590

Glu Glu Ser Gln Glu Ala Pro Glu Leu Leu Lys Arg Pro Lys Glu Tyr
            595                 600                 605

Thr Val Arg Phe Thr Phe Pro Asp Pro Pro Leu Ser Pro Val
    610                 615                 620

Leu Gly Leu His Gly Val Thr Phe Gly Tyr Gln Gly Gln Lys Pro Leu
625                 630                 635                 640

Phe Lys Asn Leu Asp Phe Gly Ile Asp Met Asp Ser Arg Ile Cys Ile
                645                 650                 655

Val Gly Pro Asn Gly Val Gly Lys Ser Thr Leu Leu Leu Leu Leu Thr
            660                 665                 670

Gly Lys Leu Thr Pro Thr His Gly Glu Met Arg Lys Asn His Arg Leu
        675                 680                 685

Lys Ile Gly Phe Phe Asn Gln Gln Tyr Ala Glu Gln Leu Arg Met Glu
    690                 695                 700

Glu Thr Pro Thr Glu Tyr Leu Gln Arg Gly Phe Asn Leu Pro Tyr Gln
705                 710                 715                 720

Asp Ala Arg Lys Cys Leu Gly Arg Phe Gly Leu Glu Ser His Ala His
                725                 730                 735

Thr Ile Gln Ile Cys Lys Leu Ser Gly Gly Gln Lys Ala Arg Val Val
            740                 745                 750

Phe Ala Glu Leu Ala Cys Arg Glu Pro Asp Val Leu Ile Leu Asp Glu
        755                 760                 765

Pro Thr Asn Asn Leu Asp Ile Glu Ser Ile Asp Ala Leu Gly Glu Ala
    770                 775                 780

Ile Asn Glu Tyr Lys Gly Ala Val Ile Val Ser His Asp Ala Arg
785                 790                 795                 800

Leu Ile Thr Glu Thr Asn Cys Gln Leu Trp Val Val Glu Glu Gln Ser
                805                 810                 815

Val Ser Gln Ile Asp Gly Asp Phe Glu Asp Tyr Lys Arg Glu Val Leu
            820                 825                 830

Glu Ala Leu Gly Glu Val Met Val Ser Arg Pro Arg Glu
        835                 840                 845

<210> SEQ ID NO 2
<211> LENGTH: 839
<212> TYPE: PRT

-continued

<213> ORGANISM: Rattus norvegicus

<400> SEQUENCE: 2

Met Pro Lys Gly Pro Lys Gln Gln Pro Pro Glu Pro Glu Trp Ile Gly
1               5                   10                  15

Asp Gly Glu Gly Thr Ser Pro Ala Asp Lys Val Val Lys Lys Gly Lys
            20                  25                  30

Lys Asp Lys Lys Thr Lys Lys Thr Phe Phe Glu Glu Leu Ala Val Glu
        35                  40                  45

Asp Lys Gln Ala Gly Glu Glu Lys Leu Gln Lys Glu Lys Glu Gln
    50                  55                  60

Gln Gln Gln Gln Gln Gln Lys Lys Lys Arg Asp Thr Arg Lys Gly
65                  70                  75                  80

Arg Arg Lys Lys Asp Val Asp Asp Asp Asp Gly Asp Glu Arg Val
                85                  90                  95

Leu Met Glu Arg Leu Lys Gln Leu Ser Val Pro Ala Ser Asp Glu Glu
            100                 105                 110

Asp Glu Val Pro Val Pro Val Pro Arg Gly Arg Lys Lys Ala Lys Gly
            115                 120                 125

Gly Asn Val Phe Glu Ala Leu Ile Gln Asp Glu Ser Glu Glu Glu Lys
130                 135                 140

Glu Glu Glu Glu Glu Lys Pro Val Leu Lys Pro Ala Lys Pro Glu Lys
145                 150                 155                 160

Asn Arg Ile Asn Lys Ala Val Ala Glu Pro Pro Gly Leu Arg Asn
                165                 170                 175

Lys Lys Gly Lys Glu Glu Lys Ser Lys Gly Lys Ala Lys Asn Lys Pro
            180                 185                 190

Ser Ala Thr Asp Ser Glu Gly Glu Asp Glu Asp Met Thr Lys Glu
            195                 200                 205

Lys Glu Pro Pro Arg Pro Gly Lys Asp Lys Asp Lys Lys Gly Ala Glu
            210                 215                 220

Gln Gly Ser Glu Glu Lys Glu Glu Lys Glu Gly Glu Val Lys Ala
225                 230                 235                 240

Asn Asp Pro Tyr Ala His Leu Ser Lys Lys Glu Lys Lys Lys Leu Lys
                245                 250                 255

Lys Gln Met Asp Tyr Glu Arg Gln Val Glu Ser Leu Lys Ala Ala Asn
            260                 265                 270

Ala Ala Glu Asn Asp Phe Ser Val Ser Gln Ala Glu Val Ser Ser Arg
        275                 280                 285

Gln Ala Met Leu Glu Asn Ala Ser Asp Ile Lys Leu Glu Lys Phe Ser
        290                 295                 300

Ile Ser Ala His Gly Lys Glu Leu Phe Val Asn Ala Asp Leu Tyr Ile
305                 310                 315                 320

Val Ala Gly Arg Arg Tyr Gly Leu Val Gly Pro Asn Gly Lys Gly Lys
            325                 330                 335

Thr Thr Leu Leu Lys His Ile Ala Asn Arg Ala Leu Ser Ile Pro Pro
            340                 345                 350

Asn Ile Asp Val Leu Leu Cys Glu Gln Glu Val Val Ala Asp Glu Thr
        355                 360                 365

Pro Ala Val Gln Ala Val Leu Arg Ala Asp Thr Lys Arg Leu Arg Leu
        370                 375                 380

Leu Glu Glu Glu Lys Arg Leu Gln Gly Gln Leu Glu Gln Gly Asp Asp
385                 390                 395                 400

Thr Ala Ala Glu Lys Leu Glu Lys Val Tyr Glu Glu Leu Arg Ala Thr

```
                    405                 410                 415
Gly Ala Ala Ala Glu Ala Lys Ala Arg Arg Ile Leu Ala Gly Leu
                420                 425                 430

Gly Phe Asp Pro Glu Met Gln Asn Arg Pro Thr Gln Lys Phe Ser Gly
            435                 440                 445

Gly Trp Arg Met Arg Val Ser Leu Ala Arg Ala Leu Phe Met Glu Pro
        450                 455                 460

Thr Leu Leu Met Leu Asp Glu Pro Thr Asn His Leu Asp Leu Asn Ala
465                 470                 475                 480

Val Ile Trp Leu Asn Asn Tyr Leu Gln Gly Trp Arg Lys Thr Leu Leu
                485                 490                 495

Ile Val Ser His Asp Gln Gly Phe Leu Asp Asp Val Cys Thr Asp Ile
            500                 505                 510

Ile His Leu Asp Thr Gln Arg Leu His Tyr Tyr Arg Gly Asn Tyr Met
        515                 520                 525

Thr Phe Lys Lys Met Tyr Gln Gln Lys Gln Lys Glu Leu Leu Lys Gln
    530                 535                 540

Tyr Glu Lys Gln Glu Lys Lys Leu Lys Glu Leu Lys Ala Gly Gly Lys
545                 550                 555                 560

Ser Thr Lys Gln Ala Glu Lys Gln Thr Lys Glu Val Leu Thr Arg Lys
                565                 570                 575

Gln Gln Lys Cys Arg Arg Lys Asn Gln Asp Glu Ser Gln Asp Pro
            580                 585                 590

Pro Glu Leu Leu Lys Arg Pro Arg Glu Tyr Thr Val Arg Phe Thr Phe
        595                 600                 605

Pro Asp Pro Pro Leu Ser Pro Pro Val Leu Gly Leu His Gly Val
    610                 615                 620

Thr Phe Gly Tyr Glu Gly Gln Lys Pro Leu Phe Lys Asn Leu Asp Phe
625                 630                 635                 640

Gly Ile Asp Met Asp Ser Arg Ile Cys Ile Val Gly Pro Asn Gly Val
                645                 650                 655

Gly Lys Ser Thr Leu Leu Leu Leu Thr Gly Lys Leu Thr Pro Thr
            660                 665                 670

Asn Gly Glu Met Arg Lys Asn His Arg Leu Lys Ile Gly Phe Phe Asn
        675                 680                 685

Gln Gln Tyr Ala Glu Gln Leu His Met Glu Glu Thr Pro Thr Glu Tyr
    690                 695                 700

Leu Gln Arg Gly Phe Asn Leu Pro Tyr Gln Asp Ala Arg Lys Cys Leu
705                 710                 715                 720

Gly Arg Phe Gly Leu Glu Ser His Ala His Thr Ile Gln Ile Cys Lys
                725                 730                 735

Leu Ser Gly Gly Gln Lys Ala Arg Val Val Phe Ala Glu Leu Ala Cys
            740                 745                 750

Arg Glu Pro Asp Val Leu Ile Leu Asp Glu Pro Thr Asn Asn Leu Asp
        755                 760                 765

Ile Glu Ser Ile Asp Ala Leu Gly Glu Ala Ile Asn Glu Tyr Lys Gly
    770                 775                 780

Ala Val Ile Val Val Ser His Asp Ala Arg Leu Ile Thr Glu Thr Asn
785                 790                 795                 800

Cys Gln Leu Trp Val Val Glu Glu Gln Ser Val Ser Gln Ile Asp Gly
                805                 810                 815

Asp Phe Asp Asp Tyr Lys Arg Glu Val Leu Glu Ala Leu Gly Glu Val
            820                 825                 830
```

Met Val Asn Arg Pro Arg Asp
            835

<210> SEQ ID NO 3
<211> LENGTH: 54
<212> TYPE: DNA
<213> ORGANISM: Artificial Sequence
<220> FEATURE:
<223> OTHER INFORMATION: Synthetic construct

<400> SEQUENCE: 3
taagctgtca tctggcttaa taaggatcct tattaagcca gatgacagct tttt         54

<210> SEQ ID NO 4
<211> LENGTH: 60
<212> TYPE: DNA
<213> ORGANISM: Artificial Sequence
<220> FEATURE:
<223> OTHER INFORMATION: Synthetic construct

<400> SEQUENCE: 4
ctagaaaaag ctgtcatctg gcttaataag gatccttatt aagccagatg acagcttaat   60

<210> SEQ ID NO 5
<211> LENGTH: 837
<212> TYPE: PRT
<213> ORGANISM: Mus musculus

<400> SEQUENCE: 5

Met Pro Lys Gly Pro Lys Gln Gln Pro Glu Pro Glu Trp Ile Gly
1               5                   10                  15

Asp Gly Glu Gly Thr Ser Pro Ala Asp Lys Val Val Lys Gly Lys
                20                  25                  30

Lys Asp Lys Lys Thr Lys Lys Thr Phe Phe Glu Glu Leu Ala Val Glu
        35                  40                  45

Asp Lys Gln Ala Gly Glu Glu Lys Leu Gln Lys Glu Lys Glu Gln
    50                  55                  60

Gln Gln Gln Gln Gln Gln Gln Lys Lys Arg Asp Thr Arg Lys Gly
65                  70                  75                  80

Arg Arg Lys Lys Asp Val Asp Asp Ser Asp Glu Arg Val Leu Met
                85                  90                  95

Glu Arg Leu Lys Gln Leu Ser Val Pro Ala Ser Asp Glu Glu Asp Glu
            100                 105                 110

Val Pro Ala Pro Ile Pro Arg Gly Arg Lys Lys Ala Lys Gly Gly Asn
        115                 120                 125

Val Phe Glu Ala Leu Ile Gln Asp Asp Ser Glu Glu Glu Glu Glu
    130                 135                 140

Glu Glu Asn Arg Val Leu Lys Pro Ala Lys Pro Glu Lys Asn Arg Ile
145                 150                 155                 160

Asn Lys Ala Val Ala Glu Glu Pro Pro Gly Leu Arg Ser Lys Lys Gly
                165                 170                 175

Lys Glu Glu Lys Ser Lys Gly Lys Ala Lys Ser Lys Pro Ala Ala Ala
            180                 185                 190

Asp Ser Glu Gly Glu Glu Glu Glu Asp Thr Ala Lys Glu Lys Glu
        195                 200                 205

Pro Pro Gln Gln Gly Lys Asp Arg Asp Lys Glu Ala Glu Gln Gly
    210                 215                 220

Ser Gly Glu Glu Lys Glu Glu Lys Glu Gly Asp Leu Lys Ala Asn Asp
225                 230                 235                 240

-continued

```
Pro Tyr Ala Asn Leu Ser Lys Lys Glu Lys Lys Leu Lys Lys Gln
            245                 250                 255

Met Asp Tyr Glu Arg Gln Val Glu Ser Leu Lys Ala Ala Asn Ala Ala
        260                 265                 270

Glu Asn Asp Phe Ser Val Ser Gln Ala Glu Val Ser Ser Arg Gln Ala
            275                 280                 285

Met Leu Glu Asn Ala Ser Asp Ile Lys Leu Glu Lys Phe Ser Ile Ser
        290                 295                 300

Ala His Gly Lys Glu Leu Phe Val Asn Ala Asp Leu Tyr Ile Val Ala
305                 310                 315                 320

Gly Arg Arg Tyr Gly Leu Val Gly Pro Asn Gly Lys Gly Lys Thr Thr
                325                 330                 335

Leu Leu Lys His Ile Ala Asn Arg Ala Leu Ser Ile Pro Pro Asn Ile
            340                 345                 350

Asp Val Leu Leu Cys Glu Gln Glu Val Val Ala Asp Glu Thr Pro Ala
        355                 360                 365

Val Gln Ala Val Leu Arg Ala Asp Thr Lys Arg Leu Arg Leu Leu Glu
370                 375                 380

Glu Glu Arg Arg Leu Gln Gly Gln Leu Glu Gln Gly Asp Asp Thr Ala
385                 390                 395                 400

Ala Glu Lys Leu Glu Lys Val Tyr Glu Glu Leu Arg Ala Thr Gly Ala
                405                 410                 415

Ala Ala Ala Glu Ala Lys Ala Arg Arg Ile Leu Ala Gly Leu Gly Phe
            420                 425                 430

Asp Pro Glu Met Gln Asn Arg Pro Thr Gln Lys Phe Ser Gly Gly Trp
        435                 440                 445

Arg Met Arg Val Ser Leu Ala Arg Ala Leu Phe Met Glu Pro Thr Leu
450                 455                 460

Leu Met Leu Asp Glu Pro Thr Asn His Leu Asp Leu Asn Ala Val Ile
465                 470                 475                 480

Trp Leu Asn Asn Tyr Leu Gln Gly Trp Arg Lys Thr Leu Leu Ile Val
                485                 490                 495

Ser His Asp Gln Gly Phe Leu Asp Val Cys Thr Asp Ile Ile His
            500                 505                 510

Leu Asp Thr Gln Arg Leu His Tyr Tyr Arg Gly Asn Tyr Met Thr Phe
        515                 520                 525

Lys Lys Met Tyr Gln Gln Lys Gln Lys Glu Leu Leu Lys Gln Tyr Glu
530                 535                 540

Lys Gln Glu Lys Lys Leu Lys Glu Leu Lys Ala Gly Gly Lys Ser Thr
545                 550                 555                 560

Lys Gln Ala Glu Lys Gln Thr Lys Glu Val Leu Thr Arg Lys Gln Gln
                565                 570                 575

Lys Cys Arg Arg Lys Asn Gln Asp Glu Glu Ser Gln Glu Pro Pro Glu
            580                 585                 590

Leu Leu Lys Arg Pro Lys Glu Tyr Thr Val Arg Phe Thr Phe Pro Asp
        595                 600                 605

Pro Pro Pro Leu Ser Pro Val Leu Gly Leu His Gly Val Thr Phe
610                 615                 620

Gly Tyr Glu Gly Gln Lys Pro Leu Phe Lys Asn Leu Asp Phe Gly Ile
625                 630                 635                 640

Asp Met Asp Ser Arg Ile Cys Ile Val Gly Pro Asn Gly Val Gly Lys
                645                 650                 655

Ser Thr Leu Leu Leu Leu Leu Thr Gly Lys Leu Thr Pro Thr Asn Gly
            660                 665                 670
```

```
Glu Met Arg Lys Asn His Arg Leu Lys Ile Gly Phe Phe Asn Gln Gln
            675                 680                 685

Tyr Ala Glu Gln Leu His Met Glu Glu Thr Pro Thr Glu Tyr Leu Gln
        690                 695                 700

Arg Ser Phe Asn Leu Pro Tyr Gln Asp Ala Arg Lys Cys Leu Gly Arg
705                 710                 715                 720

Phe Gly Leu Glu Ser His Ala His Thr Ile Gln Ile Cys Lys Leu Ser
                725                 730                 735

Gly Gly Gln Lys Ala Arg Val Val Phe Ala Glu Leu Ala Cys Arg Glu
            740                 745                 750

Pro Asp Val Leu Ile Leu Asp Glu Pro Thr Asn Asn Leu Asp Ile Glu
        755                 760                 765

Ser Ile Asp Ala Leu Gly Glu Ala Ile Asn Asp Tyr Lys Gly Ala Val
770                 775                 780

Ile Val Val Ser His Asp Ala Arg Leu Ile Thr Glu Thr Asn Cys Gln
785                 790                 795                 800

Leu Trp Val Val Glu Glu Gln Gly Val Ser Gln Ile Asp Gly Asp Phe
                805                 810                 815

Asp Asp Tyr Lys Arg Glu Val Leu Glu Ala Leu Gly Glu Val Met Val
            820                 825                 830

Asn Arg Pro Arg Asp
        835

<210> SEQ ID NO 6
<211> LENGTH: 2538
<212> TYPE: DNA
<213> ORGANISM: Homo sapiens

<400> SEQUENCE: 6
atgccgaagg cgcccaagca gcagccgccg gagcccgagt ggatcgggga cggagagagc       60
acgagcccat cagacaaagt ggtgaagaaa gggaagaagg acaagaagat caaaaaaacg      120
ttctttgaag agctggcagt agaagataaa caggctgggg aagaagagaa agtgctcaag      180
gagaaggagc agcagcagca gcaacagcaa cagcagcaaa aaaaaaagcg agatacccga      240
aaaggcaggc ggaagaagga tgtggatgat gatggagaag agaaagagct catggagcgt      300
cttaagaagc tctcagtgcc aaccagtgat gaggaggatg aagtacccgc cccaaaaccc      360
cgcggaggga agaaaaccaa gggtggtaat gttttttgcag ccctgattca ggatcagagt      420
gaggaagagg aggaggaaga aaaacatcct cctaagcctg ccaagccgga agaatcgg       480 atcaataagg ccgtatctga ggaacagcag cctgcactca agggcaaaaa gggaaaggaa      540
gagaagtcaa agggaaggc taagcctcaa aataaattcg ctgctctgga caatgaagag      600
gaggataaag aagaagaaat tataaaggaa aaggagcctc ccaaacaagg aaggagaag        660 gccaagaagg cagagcaggg ttcagaggaa gaggagaag gggaagaaga ggaggagaa        720 ggaggagagt ctaaggcaga tgatccctat gctcatctta gcaaaaagga gaagaaaaag      780
ctgaaaaaac agatggagta tgagcgccaa gtggcttcat taaaagcagc caatgcagct      840
gaaaatgact tctccgtgtc ccaggcggag atgtcctccc gccaagccat gttagaaaat      900
gcatctgaca tcaagctgga gaagttcagc atctccgctc atggcaagga gctgttcgtc      960
aatgcagacc tgtacattgt agccggccgc cgctacgggc tggtaggacc caatggcaag     1020
ggcaagacca cactcctcaa gcacattgcc aaccgagccc tgagcatccc tcccaacatt     1080
gatgtgttgc tgtgtgagca ggaggtggta gcagatgaga caccagcagt ccaggctgtt     1140
```

```
cttcgagctg acaccaagcg attgaagctg ctggaagagg agcggcggct tcagggacag    1200
ctggaacaag gggatgacac agctgctgag aggctagaga aggtgtatga ggaattgcgg    1260
gccactgggg cggcagctgc agaggccaaa gcacggcgga tcctggctgg cctgggcttt    1320
gaccctgaaa tgcagaatcg acccacacag aagttctcag ggggctggcg catgcgtgtc    1380
tccctggcca gggcactgtt catggagccc acactgctga tgctggatga gcccaccaac    1440
cacctggacc tcaacgctgt catctggctt aataactacc tccagggctg gcggaagacc    1500
ttgctgatcg tctcccatga ccagggcttc ttggatgatg tctgcactga tatcatccac    1560
ctcgatgccc agcggctcca ctactatagg ggcaattaca tgaccttcaa aaagatgtac    1620
cagcagaagc agaaagaact gctgaaacag tatgagaagc aagagaaaaa gctgaaggag    1680
ctgaaggcag gcgggaagtc caccaagcag gcggaaaaac aaacgaagga agccctgact    1740
cggaagcagc agaaatgccg acggaaaaac caagatgagg aatcccagga ggcccctgag    1800
ctcctgaagc gccctaagga gtacactgtg cgcttcactt ttccagaccc cccaccactc    1860
agccctccag tgctgggtct gcatggtgtg acattcggct accagggaca gaaaccactc    1920
tttaagaact tggattttgg catcgacatg gattcaagga tttgcattgt gggccctaat    1980
ggtgtgggga agagtacgct actcctgctg ctgactggca agctgacacc gacccatggg    2040
gaaatgagaa agaaccaccg gctgaaaatt ggcttcttca accagcagta tgcagagcag    2100
ctgcgcatgg aggagacgcc cactgagtac ctgcagcggg gcttcaacct gccctaccag    2160
gatgcccgca gtgcctgggc cgcttcggc ctggagagtc acgccacac catccagatc    2220 tgcaaactct ctggtggtca gaaggcgcga gttgtgtttg ctgagctggc ctgtcgggaa    2280
cctgatgtcc tcatcttgga cgagccaacc aataacctgg acatagagtc tattgatgct    2340
ctaggggagg ccatcaatga atacaagggt gctgtgatcg ttgtcagcca tgatgcccga    2400
ctcatcacag aaaccaattg ccagctgtgg gtggtggagg agcagagtgt tagccaaatc    2460
gatggtgact ttgaagacta caagcgggag gtgttggagg ccctgggtga agtcatggtc    2520
agccggcccc gagagtga                                                 2538
```

<210> SEQ ID NO 7
<211> LENGTH: 2990
<212> TYPE: DNA
<213> ORGANISM: Rattus norvegicus

<400> SEQUENCE: 7

```
atggacaaag tagtgaagaa aggcaaaaaa gacaagaaga ccaaaaagac gttctttgag     60
gaactggcag tggaagacaa gcaagccggg gaagaggaga aactgcagaa ggagaaggag    120
cagcagcagc agcagcagca acagaagaaa agcgagacca ccaggaaagg tcgtcggaag    180
aaggatgtgg atgatgatga tgatggtgat gagagagtgc tcatggagcg ccttaagcag    240
ctgtctgtgc cagccagtga tgaggaagat gaggtacctg tccccgtgcc ccgaggacgg    300
aagaaggcaa agggcggaaa tgttttttgaa gccctgattc aggatgaaag tgaggaggaa    360
aaagaagagg aggaagaaaa gcctgttctc aagcctgcca agccagagaa gaatcgcatc    420
aataaggccg tggctgagga gcctcctggg ctccgaaata aaagggaaa ggaggagaaa    480 tcgaaaggga agccaagaa taaaccgtct gctacagaca gtgaagggga agatgatgag    540
gacatgacta agaaaaggga gcctcccagg ccagggaagg acaaagacaa aagggagct    600 gagcagggtt cagaggaaga gaagaagag aaggaggggg aggtgaaggc gaatgatccc    660
tatgcccacc ttagcaaaaa ggaaaagaaa aagctgaaga aacagatgga ttatgaacgc    720
```

```
caggtggaat cattaaaggc agctaatgct gcagaaaatg acttctctgt gtcccaggca    780
gaggtgtctt cccgccaggc aatgttagaa aatgcatctg acattaagtt ggaaaagttc    840
agcatctcgg cccacggcaa ggagctgttt gtcaatgctg acctgtacat cgtggctggc    900
cgccgctatg ggctggtggg gcccaacggc aagggcaaga ccacacttct gaagcacatt    960
gccaaccgtg ccctgagtat cccccctaac attgatgtgc tgctgtgcga gcaggaggtg   1020
gtggctgatg aaacaccagc cgtgcaagct gttcttcgtg cagacacaaa gcgactgagg   1080
ttgctagagg aggagaaacg gcttcaggga cagctggagc aggggatga tactgccgct    1140
gagaaactag aaaaggtata tgaggaactg cgagctactg gggcagcagc tgcagaggcc   1200
aaggcacggc ggatcctggc tggcttgggc tttgaccctg agatgcagaa tcggcccaca   1260
cagaagttct ctgggggttg gcgaatgcgt gtctccctgg ccagggcact gttcatggaa   1320
cccacactgc tgatgctgga cgagcctacc aatcacctgg acctcaatgc cgtcatctgg   1380
ctcaataact accttcaggg ctggaggaag acactgctga tcgtctccca cgaccagggc   1440
tttctggatg atgtctgcac cgatatcatc cacctggaca ctcagcggct ccattactac   1500
agggcaatt acatgacctt caagaagatg taccagcaga agcagaagga gctgctgaag   1560
cagtacgaga acaggagaa gaagctgaag gagctgaagg ctgggggcaa gtccaccaag   1620
caagcggaaa agcaaacaaa ggaagtcctg actcgaaaac agcagaaatg ccgaaggaaa   1680
aaccaggatg aggagtctca ggatccccct gagcttctga gcgccccag ggagtacact    1740
gtgcgattca ccttcccaga ccccccacct ctcagcccac ctgtcctggg gctgcatggt   1800
gtgacgtttg gctacgaggg gcagaagcca ctctttaaga acctggattt cggcatcgac   1860
atggactccc gaatttgcat tgtgggtccc aatggtgtgg ggaagagcac actactcctg   1920
ttgctgactg gcaagctgac accgaccaac ggggaaatga ggaagaacca tcggctgaaa   1980
atcggcttct ttaaccagca gtatgcagag cagctgcaca tggaggagac gcccaccgag   2040
tacctgcagc ggggcttcaa cctgcctat caggatgccc ggaagtgctt gggccgcttc    2100
ggcctggaga gccacgccca caccatccag atctgcaaac tctcgggcgg gcagaaagcc   2160
cgagttgtgt ttgcggagct ggcctgtcgg gagcctgatg tcctcatctt ggatgaacca   2220
accaataact tggacataga gtccatcgat gccctgggag aggccatcaa cgagtacaag   2280
ggagctgtga tcgttgtcag ccatgatgca cgcctcatca cagaaaccaa ctgccagttg   2340
tgggtcgtgg aggagcagag tgtcagtcaa attgatggtg actttgatga ctacaagcga   2400
gaggtgttga aggccctggg tgaagtcatg gtcaaccgac tcgggattg agttcttctg     2460
gaagcctgct gtgacaagct cctatggctg gaatctaggc catctcttta tccaccaaga   2520
agcctgctgt gtctgctgcc agctgcagcc acatgggcca agaagtggcg tgttgccttg   2580
atgtgtgtga gagcatcctt ccatgtgaac tgtgtccttc tcactgaagg actgtgttcc   2640
cttgaggtaa ctgagctggc ttgcccacac tggcttagtc tctattcaga caggtgacct   2700
ttgctgtggt gggttccccc tcagacctaa ttaaggtggc ctcttgtctc gagacttttg   2760
ccactcagaa ctgaccctgg tccctccttt tggaagggta ctactgactc gctgacataa   2820
acagccagaa cctcagggct ggaggcaagt gtctgagacc tgtactgtct cacccaagat   2880
ctggtgcctg tgatcccttg tctcatgggg acttgagggc aggaaaggaa gctcctgaac   2940
tgaagtctcc tttacaaggg aggaataaag gagtgggtgc tgatacatgt              2990
```

<210> SEQ ID NO 8
<211> LENGTH: 3207
<212> TYPE: DNA

<213> ORGANISM: Mus musculus

<400> SEQUENCE: 8

| | | | | | |
|---|---|---|---|---|---|
| gcgccgctgg | aggactctta | actgccgccg | cgatgccgaa | gggtcccaag | caacagccgc | 60 |
| ccgagcccga | gtggatcggg | gacggcgagg | gcacgagccc | cgcggacaaa | gtagtgaaga | 120 |
| aaggaaaaaa | ggacaagaag | accaaaaaga | cgttctttga | agagctggca | gtagaggaca | 180 |
| aacaagctgg | ggaagaggaa | aaattgcaga | aggagaagga | gcagcaacag | caacagcagc | 240 |
| aacagaagaa | aaagcgagac | accaggaaag | gccgtcggaa | aaaggatgtg | gacgatgata | 300 |
| gtgatgagag | agtgctcatg | gagcgactta | agcaactgtc | tgtgccagcc | agtgatgagg | 360 |
| aagatgaggt | gcctgccccc | ataccccgag | gacggaagaa | ggccaagggt | ggaaatgttt | 420 |
| ttgaagccct | gattcaggat | gacagtgagg | aggaggaaga | ggaggaagaa | aaccgtgttc | 480 |
| tcaagcccgc | caagccagag | aagaatcgca | tcaataaagc | cgtggctgag | gaacctcctg | 540 |
| ggctcaggag | taaaaaggga | aaggaggaga | atcaaaagg | gaaagccaag | agtaaacctg | 600 |
| ctgctgcaga | cagtgaaggg | gaagaggagg | aggaggacac | agctaaagaa | aaggagcctc | 660 |
| ctcagcaagg | gaaggacaga | gacaaaaagg | aggctgagca | gggctcaggg | gaagagaagg | 720 |
| aagagaaaga | aggggacttg | aaggcaaacg | atccctatgc | caaccttagc | aaaaaggaaa | 780 |
| agaaaaagct | aaagaaacag | atggattatg | aacgacaggt | ggagtcattg | aaagcagcta | 840 |
| atgctgcaga | aaacgacttc | tctgtgtccc | aggcagaggt | gtcttcccgc | caggcaatgt | 900 |
| tagaaaatgc | atctgacatt | aagttggaaa | agttcagcat | ctccgcccac | ggcaaggagc | 960 |
| tattcgtcaa | tgctgacctg | tacatagtag | ccggccgccg | ctatgggctg | gtgggaccca | 1020 |
| acggcaaagg | caaaaccacg | cttctgaagc | acattgccaa | ccgtgccctg | agcatccccc | 1080 |
| ctaacattga | cgtgctgctg | tgcgagcagg | aggtggtggc | tgatgaaaca | ccagccgtgc | 1140 |
| aagctgtcct | tcgagcagat | accaagcgac | tgaggttgct | agaggaggag | agacggcttc | 1200 |
| agggacagct | ggagcagggg | gatgacactg | ctgctgagaa | actagaaaag | gtgtatgagg | 1260 |
| aactgcgagc | taccggggca | gcagctgcag | aggccaaggc | acggcggatc | ctggctggct | 1320 |
| tgggcttcga | ccctgagatg | cagaatcggc | ccacacagaa | gttctctggg | ggttggagaa | 1380 |
| tgcgtgtctc | cctggccagg | gcactgttca | tggagccaac | gctgctgatg | ttggatgagc | 1440 |
| ccactaacca | cctggacctc | aacgccgtca | tctggctcaa | taactacctt | cagggctgga | 1500 |
| ggaagacgtt | gctgattgtc | tcccacgacc | agggctttct | ggatgacgtt | tgcactgata | 1560 |
| tcatccacct | ggacacccag | cggctccatt | actacagggg | caattacatg | accttcaaga | 1620 |
| agatgtacca | gcagaagcag | aaagagctgc | taaagcagta | cgagaagcag | gagaagaaac | 1680 |
| tgaaggagct | gaaggctggg | ggcaagtcca | ccaagcaagc | ggaaaagcaa | acaaaggaag | 1740 |
| tcctgactcg | aaaacagcag | aagtgccgac | ggaaaaacca | ggatgaagag | tctcaggagc | 1800 |
| cccctgagct | cctgaagcgt | cccaaggagt | acaccgtgcg | cttcacccttc | ccagacccccc | 1860 |
| cgcctctcag | cccacctgtg | ctgggcctgc | acggtgtgac | gtttggctac | gaggggcaga | 1920 |
| agccactctt | taagaatcta | gatttcggca | tcgactgga | ctcccggatt | tgcatcgtgg | 1980 |
| gtcccaatgg | tgtggggaag | agcacactac | tcctgctgct | gactggcaag | ctgacaccga | 2040 |
| ccaacgggga | gatgaggaag | aaccatcggc | tgaaaatcgg | cttctttaac | cagcagtacg | 2100 |
| cagagcagct | gcacatggag | gagacgccca | ctgagtacct | gcagcggagc | ttcaatctgc | 2160 |
| cctaccagga | tgcccggaag | tgcttgggcc | gctttggcct | ggagagccac | gcccacacca | 2220 |
| tccagatctg | caaactctcc | ggtgggcaga | agcccgagt | tgtgtttgcg | gagctggcct | 2280 |

```
gtcgggagcc tgatgtcctc atcttggatg aaccaaccaa taacttggac atagagtcca    2340
tcgatgccct gggggaggcc atcaacgact acaaggggc tgtgatcgtt gtcagccacg     2400
atgcgcgcct catcacagaa accaactgcc agttgtgggt ggtggaggag cagggtgtca    2460
gtcagatcga cggcgacttt gatgactaca agcgagaggt gttggaggcc ctgggtgagg    2520
tcatggtcaa ccgtcctcgg gattgagctc cctcctggaa gctgctgcaa ccagctccta    2580
tggctggagt ctaggccgtc tcccctcatc cacctagaag cctgctgcaa ccagctccta    2640
cggctggagt ctaggccgtc tcccctcatc cacctagaag cctgccatgg ctgctgccag    2700
ctgcagcagc cacataggcc atgaaggtgg cgtgttgcct tgatgtgtgt gagagcatcc    2760
atccgtgtgg attgtgtcct tctcaatgaa ggactgtgtt cccttgagg taactgagct     2820 ggcttgccca cactggctca gtctcttcag aaagaggtga cctttgctgt gctgggttcc    2880
cctcaggcct agttaaggtg gcctcttgtc tcaagacctt tgccactcag aactgaccct    2940
ggtccctcct tttggaaggg tactactgac tcactgacac aaacagccag aacctcaggg    3000
ctggaggcaa gtgtctgaga cctggactgt ttcaccaaag atctggtgcc tgtggtccct    3060
tgtctcgtgg ggacttgagg gcaggaaagg agaactctag aactgaagtc tcctttacag    3120
gggaggaaat aaagtagtgg ggtgctgaca aaaaaaaaaa aaaaaaaaaa aaaaaaaaaa    3180
aaaaaaaaaa aaaaaaaaaa aaaaaaa                                       3207

<210> SEQ ID NO 9
<211> LENGTH: 33
<212> TYPE: DNA
<213> ORGANISM: Artificial Sequence
<220> FEATURE:
<223> OTHER INFORMATION: Synthetic construct

<400> SEQUENCE: 9
atcccgggat gccgaaggcg cccaagcagc agc                                 33

<210> SEQ ID NO 10
<211> LENGTH: 30
<212> TYPE: DNA
<213> ORGANISM: Artificial Sequence
<220> FEATURE:
<223> OTHER INFORMATION: Synthetic construct

<400> SEQUENCE: 10
atctcgagtc actctcgggg ccggctgacc                                     30
```